United States Patent
Campbell et al.

(10) Patent No.: US 6,208,974 B1
(45) Date of Patent: Mar. 27, 2001

(54) METHOD AND SYSTEM FOR MANAGING WELLNESS PLANS FOR A MEDICAL CARE PRACTICE

(75) Inventors: Scott Douglas Campbell, Portland, OR (US); Mark Howard, Vancouver, WA (US)

(73) Assignee: Medical Management International, Inc., Portland, OR (US)

( * ) Notice: Subject to any disclaimer, the term of this patent is extended or adjusted under 35 U.S.C. 154(b) by 0 days.

(21) Appl. No.: 09/000,602

(22) Filed: Dec. 30, 1997

(51) Int. Cl.[7] .......................... G06F 17/60; G06F 159/00
(52) U.S. Cl. ......................................... 705/3; 705/2
(58) Field of Search ................... 705/1, 2, 3, 4

(56) References Cited

PUBLICATIONS

Maroney, Martha, "Leapin' Lizards: Business Solution I," *Microsoft Developer Network News*, May/Jun., 1995.

Brochure, "Client–Server Solutions–Vetsmart," ©*Microsoft Corporation 1994*.

Brochure, "Client–Server Solutions–Vetsmart," ©*Microsoft Corporation 1995*.

*Primary Examiner*—Eric W. Stamber
*Assistant Examiner*—Hani. M. Kazimi
(74) *Attorney, Agent, or Firm*—Klarquist Sparkman Campbell Leigh & Whinston, LLP

(57) ABSTRACT

Wellness plan administration software provides a user interface to enable users to learn about and select a wellness plan. The software tracks wellness plan service items for patients and dynamically estimates discounts for service items offered to patients during visits to a medical facility. When a patient's visit is complete, the software can generate an invoice automatically and analyze the product and service items provided during the visit to determine the appropriate discount. The software includes additional features for recording promotional activities associated with wellness plans and computing employee bonuses.

11 Claims, 13 Drawing Sheets

FIG. 3

Examination Room Status — 300

Mary Louden — Coal — M — Canine - Retriever Labrador
Basic — Age 6 months — 80.00 lbs — 302

Presented Complaint
- Service Category: Preventative Care
- Service Perscription: Vaccinations/Deworming — 304

306

Doctor

Video

Time In: 10:54:44 — 310
Elapsed: 00:01
☐ Exam Room — 312

[Ready For Check Out] — 320    [Exit]

FIG. 4 — 400

Physical Condition

Susan Singleton — Willie — MN — Canine - Shih Tzu
Age 6y/10m — 12.00 lbs — 402

Presenting Complaint
- Service Category: Preventative Care
- Service Description: Vaccination/Deworming — 404
- Further Description: Check Ears Preventative Care — 406
- ☐ - due now
- ☐ - due soon
- ☐ - ordered
- ☐ - don't give
- ☐ - current
- ☐ Canine Cough/Bordete*
- ☐ Corone Virus
- ☐ Distemper Combination
- ☐ Heartworm Antibody
- ☐ Intestinal Parasite Fecal
- ☐ Lyme Disease
- ☐ Parvo Virus
- ☐ Rabies Virus
- ☐ Thyroid Test - reference Tentative Diagnosis History — 408
None ☐ Overall Condition
☐ Coat And Skin
☐ Ocular
☐ Otic
☐ Oral/Nasal
☐ Respiratory
☐ Cardiovascular
☐ Prodeminal
☐ Urogenital
☐ Perineal
☐ Musculoskeletal
☐ Neurological
☐ Behavioral — 410

[Exam Check-Out] — 412   [Suspend Exam] — 414   [Exam Completed] — 416   420

FIG. 11

| Estimate | | |
|---|---|---|
| Shandra Hillman | | |

| | | |
|---|---|---|
| Office Visit: Wellness Plan 1.x | To Do | Princess |
| Opthalmic Exam - complete | To Do | Princess |
| Opthalmic Exam - complete | To Do | Princess |
| Oteoscopic Exam - complete | To Do | Princess |
| Oteoscopic Exam - complete | To Do | Princess |
| Oteoscopic Exam - complete | To Do | Princess |
| Ear Cleanup - brief | 5.89 | To Do Princess |
| Ear Cleanup - brief | 5.89 | To Do Princess |
| Ear Cleanup - brief | 5.89 | To Do Princess |
| Intestinal Parasite Fecal Exam | | To Do Princess |
| Ear Swab & Microscopic Exam | 14.82 | To Do Princess |
| Ear Swab & Microscopic Exam | 14.82 | To Do Princess |
| Ear Swab & Microscopic Exam | 14.82 | To Do Princess |

| Therapy | | | |
|---|---|---|---|
| Shandra Tillman | Princess | FS | Feline - DSH |
| Basic | Age: 6y/9m | 10.00 lbs | |

View:
- ● All
- ○ To Do
- ○ Done

| Description | Rcv'd Dt | Qty Status | Dosage & Freq |
|---|---|---|---|
| Intestinal Parasite Fecal | / / | 1 To Do | |
| Office Visit: Wellness P1 | / / | 1 To Do | |
| Physical Exam: Wellness P | / / | 1 To Do | |

[Make All Done] 1208
[Print Labels] 1210
[Remove Items] 1212

Tentative Diagnoses:
| | | |
|---|---|---|
| 11/23/96 Conjunctivitis | Needs protocol | |
| 05/29/96 Dental Calculi | Client Postponed | |

[ ] [Physical Exam] [ ] [Continue]
1220  1222  1224  1226

1200, 1202, 1204, 1206, 1214

METHOD AND SYSTEM FOR MANAGING WELLNESS PLANS FOR A MEDICAL CARE PRACTICE

FIELD OF THE INVENTION

The invention relates to a computer-implemented method for managing and enrolling new clients in wellness plans.

BACKGROUND OF THE INVENTION

With rising health care costs, it is imperative that health care providers provide health services efficiently and cost effectively. At the same time, the administrative demands of medical record keeping, billing and managing a medical practice have become more burdensome. In particular, health care providers must be thorough and keep detailed records of medical exams to accurately document observations and services that have been provided.

One health care product growing in popularity is a wellness plan. The principal objective of a wellness plan is to keep a patient well. A wellness plan provides a way for a patient to pre-pay or pay on a schedule for medical services. Under a typical plan, the patient is entitled to preventative care services and discounts on other types of medical services. By establishing periodic visits at least once a year, wellness plans enable health problems to be identified and treated early. It is generally understood that the cost of healthcare rises exponentially the longer a health problem is postponed. Thus, wellness plans can drastically reduce healthcare costs by encouraging office visits that help identify and resolve health problems early.

While wellness plans are an effective means for keeping patients healthy, they are difficult and costly to administer and promote. As such there is a need for a more effective approach to managing wellness plans.

SUMMARY OF THE INVENTION

The invention is directed to a method and system for managing wellness plans for a medical care practice. While specifically adapted to a veterinary practice, the invention can be applied to other types of medical practices as well.

The invention is implemented in software that provides an interactive user interface and maintains patient, client and employee records associated with wellness plans. In this implementation, the software presents an interactive user interface that enables members of a provider team to help clients select from among a variety of wellness plans. Each of the plans is represented in memory as a set of predetermined product and service items and plan discounts. Once the client has accepted a wellness plan, the software updates the patient's records to include a list of the service items covered by the selected plan.

The wellness plan software is integrated with software used to manage a patient visit to a medical facility. This software is used to track the service and product items provided to a patient. As items are provided to a patient, the items are also recorded in memory. The software can generate cost estimates based on the service items provided to the patient during a visit, including an indicator of the cost savings due to the wellness plan. When the visit is complete, the software generates an invoice and checks whether selected service items are wellness plan items. If they are covered under the patient's plan, the software applies the discounts under the plan to the selected service items.

The wellness plan software also tracks promotional activities of provider team members. When the software detects a program action associated with promotion of a wellness plan, it records an event identifying the provider responsible for the event. These events are recorded and evaluated to compute bonuses for the providers.

Another aspect of the wellness plan software is that also performs a variety of billing and accounting related functions. A typical medical facility equipped with the software has a computer network that executes software for managing patient visits and keeping patient records. This network is linked with a central computer that automatically handles billing, collection and account maintenance functions. When a new plan is established at the facility, a server computer communicates plan contract and billing information to the central computer. From this information, the central computer determines when bills are due and produces a payment file of debit and credit card transactions that it sends electronically to a bank for payment. The central computer notifies the respective medical facilities about the status of the accounts, including, for example, indicating when a patient's account is overdue.

Additional features and advantages of the invention will become more apparent from the following detailed description and accompanying drawings.

BRIEF DESCRIPTION OF THE DRAWINGS

FIG. 3 is an example of a status screen used to check the status of a patient in the hospital.

FIG. 4 is an example of a physical exam overview display generated by an implementation of the invention.

FIG. 5 illustrates an example of an interactive physical exam display used to record information about a patient's overall condition.

FIG. 6 illustrates an example of a supplemental user interface screen that is triggered in response to an abnormal observation to prompt the user for additional input related to the abnormal observation.

FIG. 11 is an example of an interactive user interface screen used to display an estimate of the cost of services to be provided or already provided to a patient.

FIG. 12 is an example of an interactive user interface screen used to manage the administration of a service item under a treatment protocol.

DETAILED DESCRIPTION

Introduction

Figure 1:
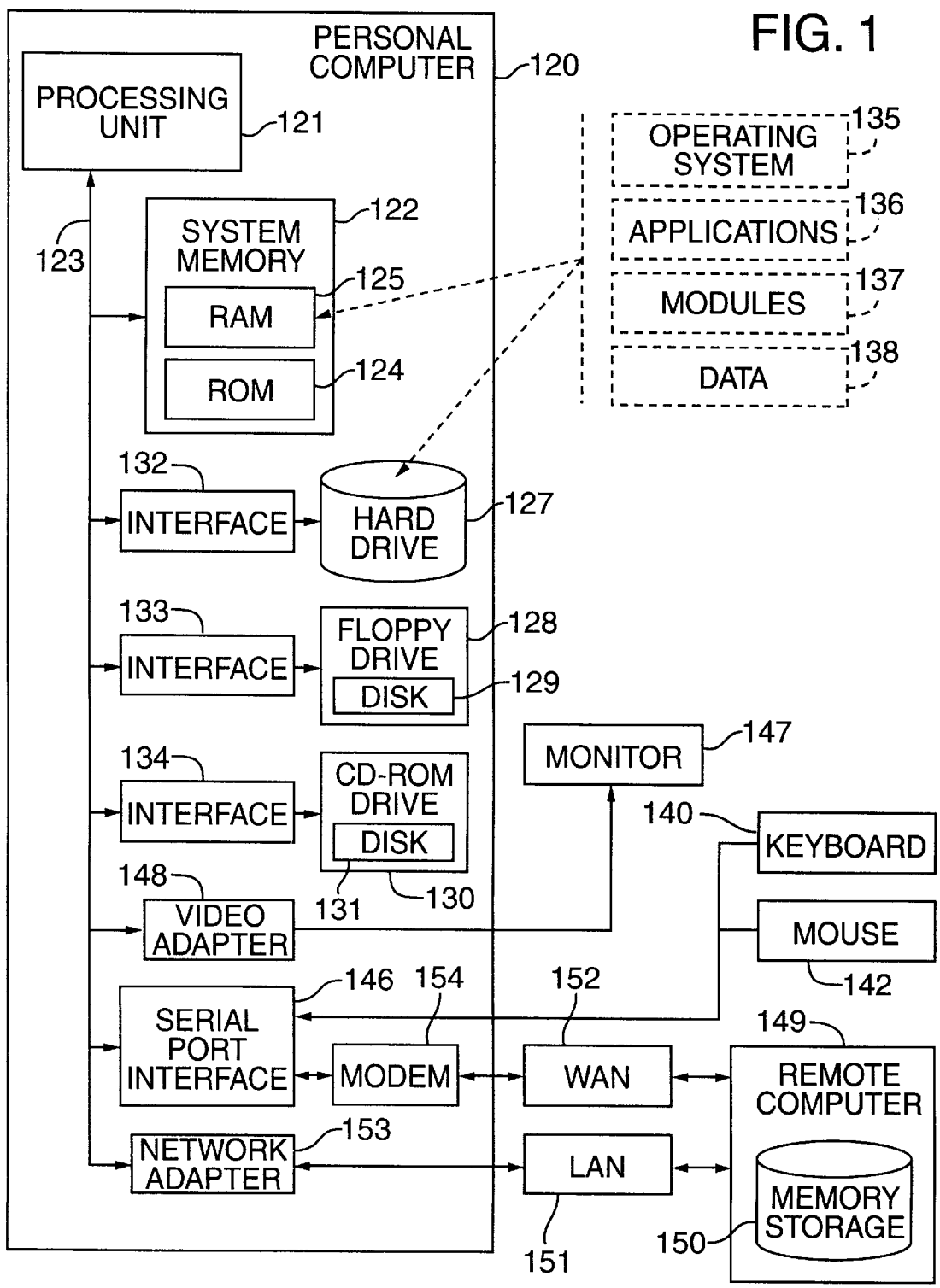
FIG. 1 is a block diagram of a computer that serves as an operating environment for medical office management software.

The invention is directed toward a method and system for managing wellness plans for a medical care practice. The specific implementation described below is a software system that manages wellness plans for a veterinary practice. Under a wellness plan, a client pays a fee in exchange for discounts on product and service items provided by a medical care provider. The wellness plan software has a user interface that provides information about wellness plans and enables a user to enter information necessary to set-up a plan. The wellness plan software then administrates the plan by handling billing and contract renewal, calculating cost estimates during office visits and applying plan discounts to products and services provided to the client.

The wellness plan software is integrated with medical management software that manages a variety of aspects of a veterinary practice, including controlling client and patient work flow in a hospital, guiding hospital personnel through medical examinations and storing medical records. The medical management software provides an effective forum for implementing wellness plans because it allows the client to see the cost savings achieved under a plan as products and services are being offered during a visit. It also facilitates promotion of the plan and tracking of wellness plan marketing by hospital employees.

Because of the relationship between the wellness plan and the medical practice management software, the following sections describes both of these components in detail. The following section begins with a description of the computer system used to execute the software. Later sections then describe an implementation of the software for managing a medical practice. The final sections describe an implementation of the wellness plan software.

System Architecture

One implementation of the system is developed for a network computing environment in a veterinary hospital. This system comprises a series of program modules running in a Windows NT® operating system environment. The program modules are implemented in the FoxPro® database programming environment. In a typical configuration, the program modules of the system are organized in a client server architecture. Several computers throughout the hospital are equipped with client software, which can access server software on a server via the network. The client software typically provides a graphical user interface comprising a number of screens in a windowing environment for prompting the user for input and displaying output.

In one particular client server implementation, the server executes database management software and maintains a series of relational databases (tables). The client and server software is developed using the FoxPro® database development tools. The client-server software is written in FoxPro® database developement environement for the Windows NT® operating system, and uses the native FoxPro database file structures.

The server software coordinates communication among the client computers, manages a database of client and patient data, monitors data supplied via the client computers, performs data processing functions on the data as observations are made, and dynamically updates the display data displayed on the client computer. While the preferred implementation for a hospital setting is a network environment, many of the software functions, including the user interface and data management functions can be performed on a single computer.

FIG. 1 and the following discussion are intended to provide a brief, general description of a suitable computing environment for the server and client computers. As noted above, the system software is implemented in a series of program modules, comprising computer executable instructions executed either on a server or client computer. Generally, program modules include routines, programs, components, data structures, etc. that perform particular tasks or implement particular abstract data types. The medical system software of the invention may be ported to other computer system configurations, including hand-held devices, multiprocessor systems, microprocessor-based or programmable consumer electronics, minicomputers, mainframe computers, and the like.

The invention is typically practiced in distributed computing environments where tasks are performed by remote processing devices that are linked through a communications network. In a distributed computing environment, program modules may be located in both local memory of a client computer and remote memory such as in the server computer.

FIG. 1 illustrates an example of a computer system that serves as an operating environment for the invention. The computer system includes a personal computer 120, including a processing unit 121, a system memory 122, and a system bus 123 that interconnects various system components including the system memory to the processing unit 121. The system bus may comprise any of several types of bus structures including a memory bus or memory controller, a peripheral bus, and a local bus using a bus architecture such as PCI, VESA, Microchannel (MCA), ISA and EISA, to name a few. The system memory includes read only memory (ROM) 124 and random access memory (RAM) 125. A basic input/output system (BIOS), containing the basic routines that help to transfer information between elements within the personal computer 120, such as during start-up, is stored in ROM 124. The personal computer 120 further includes a hard disk drive 127, a magnetic disk drive 128, e.g., to read from or write to a removable disk 129, and an optical disk drive 130, e.g., for reading a CD-ROM disk 131 or to read from or write to other optical media. The hard disk drive 127, magnetic disk drive 128, and optical disk drive 130 are connected to the system bus 123 by a hard disk drive interface 132, a magnetic disk drive interface 133, and an optical drive interface 134, respectively. The drives and their associated computer-readable media provide nonvolatile storage of data, data structures, computer-executable instructions (program code such as dynamic link libraries, and executable files), etc. for the personal computer 120. Although the description of computer-readable media above refers to a hard disk, a removable magnetic disk and a CD, it can also include other types of media that are readable by a computer, such as magnetic cassettes, flash memory cards, digital video disks, Bernoulli cartridges, and the like.

A number of program modules may be stored in the drives and RAM 125, including an operating system 135, one or more application programs 136, other program modules 137, and program data 138. A user may enter commands and information into the personal computer 120 through a keyboard 140 and pointing device, such as a mouse 142. Other input devices (not shown) may include a microphone, joystick, game pad, satellite dish, scanner, or the like. These and other input devices are often connected to the processing unit 121 through a serial port interface 146 that is coupled to the system bus, but may be connected by other interfaces, such as a parallel port, game port or a universal serial bus (USB). A monitor 147 or other type of display device is also connected to the system bus 123 via an interface, such as a video adapter 148. In addition to the monitor, personal computers typically include other peripheral output devices (not shown), such as speakers and printers.

The software system of the invention is typically implemented in a network configuration in a veterinary hospital, though it can be implemented on a single PC. In network installations, there are several personal computers like the one depicted in FIG. 1. Each of the personal computers (such as PC 120) operate in a networked environment using logical connections to one or more remote computers, such as a remote computer 149. The remote computer 149 is usually a server, but can also be a router, a peer device or other common network node. The remote computer includes many or all of the elements described relative to the personal computer 120, although only a memory storage device 150 has been illustrated in FIG. 1. The logical connections depicted in FIG. 1 include a local area network (LAN) 151 and a wide area network (WAN) 152. Such networking environments are commonplace in offices, enterprise-wide computer networks, intranets and the Internet.

When used in a LAN networking environment, the personal computer 120 is connected to the local network 151 through a network interface or adapter 153. When used in a WAN networking environment, the personal computer 120 typically includes a modem 54 or other means for establishing communications over the wide area network 152, such as the Internet. The modem 154, which may be internal or external, is connected to the system bus 123 via the serial port interface 146. In a networked environment, program modules depicted relative to the personal computer 120, or portions of them, may be stored in the remote memory storage device. The network connections shown are examples only and other means of establishing a communications link between the computers may be used.

Figure 2:
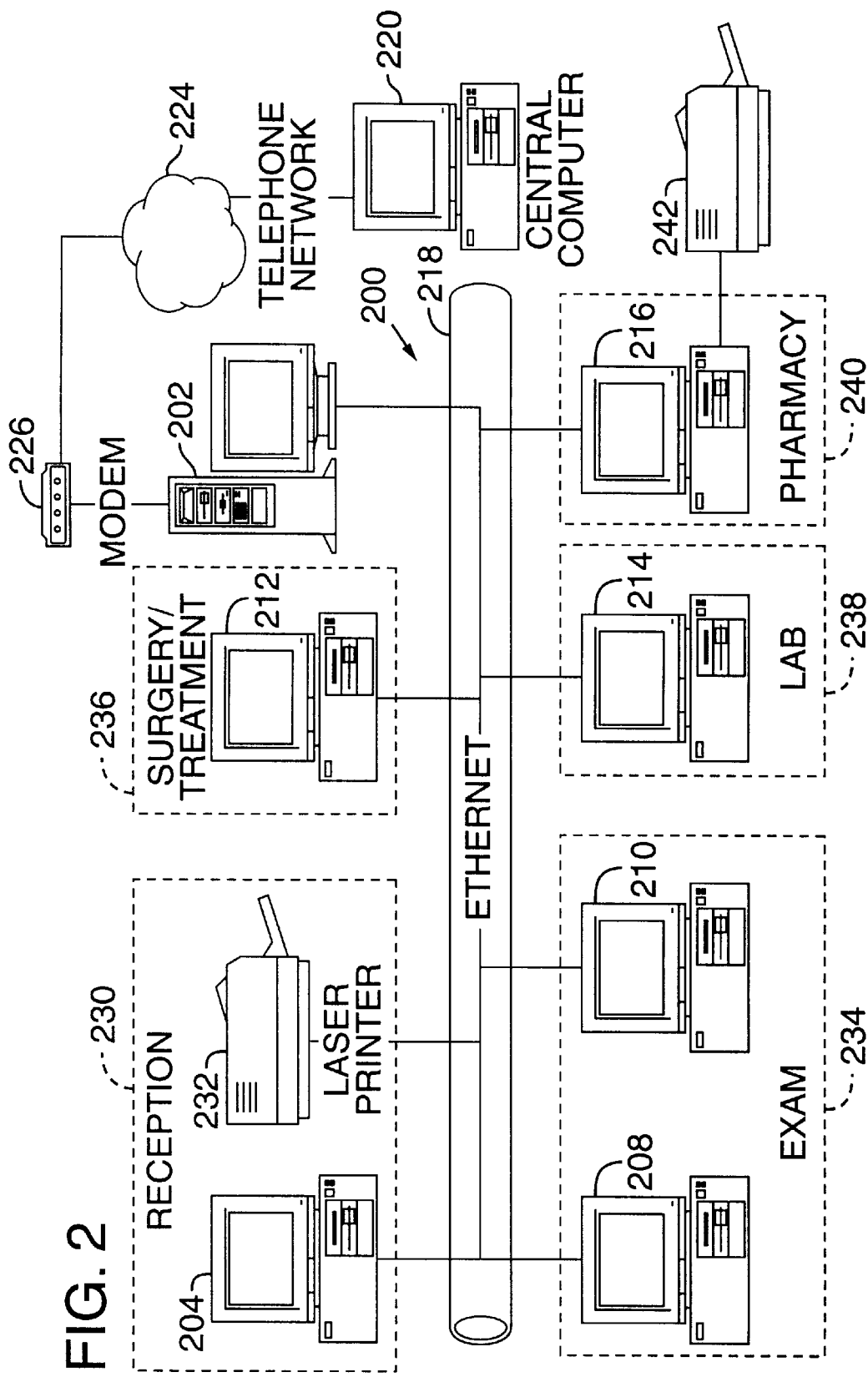
FIG. 2 is a block diagram illustrating a computer network for managing client and patient medical data in a veterinary hospital.

FIG. 2 is a block diagram illustrating a typical network configuration 200 used to implement system software of the invention in a veterinary hospital. The network configuration 200 includes a server computer 202 and a number of personal computers 204–216 connected together on a computer network 218. In this configuration, the network is an ethernet network, but any other conventional computer network can be used to implement the system. The computers are distributed throughout the hospital and are designed to provide access to some common functions as well as some special purpose functions unique to the particular computer. Some of the client computers have special attributes that enable them to perform functions relevant to the part of the hospital where they are located: 1) the reception computer 204 checks clients and patients in and out of the office and handles billing functions; 2) the exam room computers 208–210 are used by doctors and nurses to conduct medical examinations, to make diagnoses, and select a treatment protocol; 3) surgery/treatment computers 212 are located at surgery and treatment areas in the hospital and provide patient status data (e.g., traffic control, patient triage information such as names of patients, status, presenting complaint, to-do lists) as well as similar functions as the exam room computers 208–210; 4) the lab computer 214 interfaces with lab equipment and is used to enter information from lab tests; and 5) the pharmacy computer 216 is used to fill prescriptions, conduct inventory control on pharmaceuticals and medical supplies, order supplies, and provide database search functions.

While each computer is designed to perform certain types of functions in the office, many of the computers have common features and provide access to the same client and patient information and server functions. For example, if authorized, a doctor can look up client information on any of the computers in the network.

Communication Among Client Nodes

Each of the computers can transfer messages to each other via a queue on the server. When the client software running on a computer in the network wishes to communicate with other client software, the client sends a message to the server. The message can indicate that some event has taken place or it can request an action. The server places this message in a shared queue in main memory on the server.

Each of the client computers and the server periodically scan the queue for messages. In this implementation, the queue is a database file, and the clients scan the queue by performing a database query on the file. If a client finds that one of the messages is intended for it, it performs the requested action sought in the message. When the requested action is processed, the server deletes the record requesting the action. By updating the queue in this manner, each of the clients on the network are informed that the event or requested action in the message has been processed.

Authenticating Access to Server Functions and Data

The server's database management software manages access to server functions and data in the databases by authenticating access to databases or functions on the data. Specifically, the server 202 maintains a table that lists computers and users indexed to data and functions that the computer or user can access. Another authentication table tracks provider teams, which are typically comprised of a doctor, nurse and receptionist. This table keeps track of who is logged into the system and determines, based on who is logged in, what functions and data each person will be able to access. For example, if a nurse is checked in, the nurse will be able to make preliminary medical observations, but will not be able to access diagnostic screens and make diagnosis.

The server controls access to server functions and data via a table indicating the name of each client computer connected to the network and a list of functions that each client is able to access. In this particular implementation, the server uses the Windows operating system computer name to identify each computer. The server maintains a table of all computers which are attached to the system. This table includes the specific functions which the client computer is intended to perform. This enables the server to control which functions each client is able to access.

The client server model enables the provider teams to work together on a common set of data. As a member of a team completes part of an exam or conducts some treatment using the system, the server software dynamically updates the data so that it will be properly reflected to other users when they access it. For example, if a lab technician enters the test results of a blood test on the lab computer, a doctor in the exam room will be able to get this information via the exam room computer.

In the current implementation of the system, the client computers each present a graphical user interface in a windowing environment. The user interface displays text and graphical information about clients and patients (the client's pets) in windows. The users of the system enter input using a variety of input devices including a key board and pointing devices such as a mouse, trackball, touch screen membrane or touch pad.

The Link to a Remote Computer

The computer network shown in FIG. 2 is an example of the network configuration in a typical hospital. A number of these network configurations around the country are connected to a central computer 220. As shown in FIG. 2, the server computer 202 is connected to a remote computer 220, which acts as the central computer for several hospitals. The central computer periodically dials-up the server via the telephone network 224 and obtains a copy of the hospital's data All information at the hospitals which has changed is gathered into the central system.

The server, in this example configuration shown in FIG. 2, is connected to the phone network via a modem 226. The central computer 220 also controls administrative and billing functions. One important function of the central computer is how it administrates wellness plans. Specifically, the central computer is responsible for handling billing of clients that have selected wellness plans.

The Reception Computer

As introduced above, the functions of each of the client computers are generally related to where they are located in the hospital. In the receptionist area 230 of the hospital, the receptionist computer 204 is designed primarily to check patients in and out of the hospital and monitor client and patient traffic by keeping track of who is in the hospital, where they are, and how long they have been in the hospital. Typically there are at least two reception computers. Each them share a printer 232 used to print invoices and client education information.

The Exam Room Computers

In the exam rooms 234 of the hospital, the exam room computers 208–210 are used to conduct medical exams. The physical exam software modules walk the nurse and doctor through an entire medical exam. The software displays exam screens that prompt the user for input. The user interface screens guide the user by displaying a list of items that require observation. For some items, the software will not allow the user to proceed without entering an observation. At the end of the physical exam, the physical exam software requires the doctor to sign off on the physical exam. The doctor can then proceed to invoke the diagnosis software.

The diagnosis software uses the observations made during the medical exam to prepare a rule out list and prescribe a treatment protocol. Diagnosis software running on the server uses the observations to generate a list of abnormal observations and tentative diagnosis. The doctor can then select a tentative diagnosis by positioning the cursor over a diagnosis and selecting it. By selecting a tentative diagnosis, the user triggers the generation of a treatment protocol. This treatment protocol can then be integrated into future medical exam sessions. It is integrated because procedures that need to be performed and observations that need to be made are identified in the graphical exam screens in follow-up visits. Thus, once a treatment protocol is selected, the system manages the administration of that protocol in future exam sessions.

The Surgery and Treatment Computers

In the example shown in FIG. 2, the surgery and treatment computers 212 are combined and are depicted as being in a single location 236 (e.g., a surgery and treatment area in the hospital). As emphasized above, it is not necessary to have separate computers for performing separate functions such as having a surgery computer for displaying triage information or a treatment computer for recording treatments on a patient as they are performed. Instead, surgery and treatment functions can be accessed from a single computer.

The Lab Computer

In the lab 238 of the hospital, the lab computer is used to check lab tests that have been ordered and to enter lab results. The lab functions of the system include an interactive user interface that enables members of a provider team to look up a patient and either enter lab results or view a list of tests that need to be performed for a patient. The user interface includes a laboratory screen, listing records including client name, patient name, name of a test, and when the test was ordered. The user can click on a record to select it and then proceed to a lab results screen by clicking on a button in the lab screen. The system will display a lab results screen, which prompts the user to type in the results and record the changes. When the user clicks on a button to record the changes, the changes get updated in a table used to store laboratory results and symptoms maintained for the patient.

The service items ordered for a patient, such as lab tests, are recorded in an accounting line item table. When a user enters a change in status for a lab test, the system updates the status of the service item corresponding to this test in the accounting line item table. In addition to updating the status in the accounting line item table, the system posts a note in the medical lab notes for the patient indicating that the test is complete.

The Pharmacy Computer

In the pharmacy 240 of the hospital, the pharmacy computer 216 manages the pharmaceutical products and processes requests for prescriptions. The pharmacy computer executes client pharmacy software that is integrated with the exam software in that it responds to requests to generate labels when a doctor enters a prescription in a prescription screen during the medical exam. The pharmacy computer 216 is connected to a printer 242 used to print prescription labels.

Having described the system architecture of a network configuration in a veterinary hospital, we now describe the software for managing a medical practice in more detail.

Tracking the Provider Team

The software system tracks user input to the system based on a provider team. As described above, users get access to the system and its functions based on their login name. Once logged in, a user has access to data and functions in the system. As observations are entered, these observations are attributed to the person that made them based on the login of the session. A session refers to the time period in which a user is logged in to the system and is accessing server functionality. As a member of the medical team takes an action and records this action through the user interface client, the system attributes the action to the person and team that took the action.

Tracking the provider team has implications on generating billing reports and productivity reports. In the system, activities of team members can be classified as a selling or providing. As products or services are provided to a client/patient, a member of the team enters the information on the user interface, typically by selecting the item on the user interface. These items are added to a file representing the client's bill and in addition are attributed to the provider team. Chargeable service or products provided by the team are attributed to a selling and providing person in a predetermined proportion, such as 55/45 percent. This enables the system to generate productivity reports for a provider based on individual product and service items. This feature also enables the system to give credit to the providers that are responsible for getting clients to sign up on a wellness plan, which is also administered on the server.

Tracking Patient Workflow

In addition to guiding a user through the physical exam and diagnosis process, the system also tracks the work flow in a medical facility such as a hospital or doctor's office. When a patient arrives, the patient is "checked into" the system. Throughout the visit, the system tracks the patient's progress through various stages of the visit, such as waiting in the lobby, undergoing a physical examination in an exam room, awaiting check-out, undergoing tests in the lab, hospitalized, etc. These stages generally correspond to different parts of the medical facility such as the lobby, exam room, lab, surgery room etc. However, it is important to emphasize that the stages do not have to be associated with separate physical locations, especially in a smaller facility where a single room is used for the medical exam, lab tests and surgery.

As the patient progresses through a visit, the system software guides the provider team through the visit by prompting the user for input needed to complete each stage. This input can include patient data, medical findings (or at least confirmation that examination is complete), or authorization from a doctor. When a member of the provider team completes a stage in the visit, such as checking in a patient or conducting a medical exam, the system tracks the flow by updating the status of the patient's visit in memory. In a client server configuration, this status information is maintained on the server so that members of the provider team can check the patient's status from different client computers. By tracking patient status in this manner, the system ensures that the patient's visit proceeds in an orderly manner, that all necessary services are provided, and that a complete record of an entire visit is recorded in the system. In addition, it gives the provider team an opportunity to track which patients are in the facility, what their current status is, and how long each patient has been in the facility.

Patient Check In

When a client brings a patient to the veterinary hospital, the first step on the system is to check-in the client and patient at the receptionist computer. The receptionist computer acts as an interface to the systems Appointment Scheduler and also provides a Reception screen that enables the user to change the status or location of patients within the hospital, as tracked by the server. The receptionist performs several tasks using the reception screen as a method of identifying the patient to service. These functions include checking patients into the hospital, assigning exam rooms, making appointments, making follow-up telephone calls, and performing patient check-out and cash receipts functions.

The reception screen is used to check in a client and the patient (the client's pet). If either the client of patient is new, the system presents screens to prompt the user for missing information. For patients, the system prompts the user for patient information such as: gender (male, female, unknown), whether neutered or spayed, noting of allergic reaction, tendency of a pet to bite, and whether pet is on wellness plan.

As part of the client check in procedure, the system may request the client to verify client information. At a client check in screen, the system will check whether the client has been in the hospital in the last 15 days. If so, the system will assume that the client information displayed in this screen is current. If not, the client screen will prompt the user to verify client information. The receptionist must enter input acknowledging that the client has signed a release to provide care to the patient. The entry of the release to the system is a critical event that must occur before the system will proceed to a medical exam. The receptionist can also enter a list of items that the client left with the pet. This information is useful at a check out screen, where the reception computer retrieves a list of these items from the server and displays them as reminder to return them to the client.

As part of the patient check in procedure, a receptionist enters the presenting complaint via the user interface of the reception computer. The reception computer sends the text describing the presenting complaint to the server, which in turn records it in the patient's medical record. A new medical record, with presenting complaint, is created for each visit of the patient to the hospital. Client computers load and display the presenting complaint (as well as other patient data) in a banner displayed in a variety of screens in client computers in the hospital when accessed by members of the provider team. The receptionist also enters the patient's weight and records the weight in the system. The entry of the weight information is another critical event that needs to occur before any exam or procedure can occur on the patient during the visit. For example, the system will not allow a user to execute the physical exam software for this patient without having this information recorded first.

When a user enters a request at a client computer to load physical exam software for a patient, the client computer sends the request to the server. The server checks the patient's data file to check whether a critical event (entry of the weight) has occurred. If not, the server will transfer a message to the client computer indicating the error and the reason for the error. The client computer will then display a message box to the user indicating that the critical event must occur before the physical exam can proceed.

A main control screen, accessible from the receptionist computer, tracks the status of patients relative to the traffic at the hospital. The server classifies patients as 1) Awaiting Pick Up, 2) Checking Out, 3) Missed Appointments, 4) In the Lobby, and 5) Scheduled to come in. Category 4 is broken into two further categories, using attributes assigned to the record in a traffic database: A) Scheduled to Come In, Drop Off; and Scheduled to come In, In Lobby.

This feature is implemented by dynamically tracking the patients in a hospital in a file on the server. The server maintains patient status table storing a dynmanic list of all patients which are in the hospital at a given time. This table also includes the date and time the patient arrived, and the current physical location of the patient within the hospital. The server updates the table in response to messages from the clients that change the status of the patient. For example, when the reception computer checks in a patient, it also sends a message to the server indicating the name and status of the patient. The server places a time stamped record in the patient status table. As the patient proceeds through the hospital from reception, exam room, to check out, the client computers update the status of the patient by sending a message to the server indicating the patient and the current patient status.

Automatic Selection and Playback of Client Education Video

The system is programmed to playback client education videos for clients in the waiting room of the hospital. There are two ways to select a video in the system. One way is for the receptionist to select a video from a list. In this case, the receptionist specifies the video, the exam room, and a programmable delay period. In response, the server issues a command to the exam computer to queue the video and play it after the programmed delay period. The video is preferably stored on the client computer (e.g., the exam room computer) where it will be played back. The video will begin to play on the exam room computer after the delay period chosen by the receptionist elapses.

The second way to playback a video in the system is by automatic selection by the server. The server matches the patient in the hospital with a room where the patient is located using two tables: 1) the patient status table, which shows the patients currently in the hospital and each of the patients' current status; and 2) a client computer table, which maintains the status and identification of each computer in the hospital. When the patient is assigned to an exam room, the system matches the patient to the computer associated with that exam room. The server then evaluates a variety of attributes about the patient to select an appropriate video. One attribute is a patient record indicating the purpose of the visit. Other attributes used to select a video are the type of pet, the age of the pet, and the time of year. The server first tries to find a matching video for the purpose of the visit by text searching the list of videos for a topic that matches the purpose of the visit. Finding no matches, the server continues searching for matches based on other criteria in a predetermined order.

Physical Examination

Transferring from One "Room" to Another

Before the physical exam can begin, the receptionist has to check the patient into an exam room. The receptionist does this by entering the exam room number at the reception computer. The reception computer sends a message to the server, which in turn, updates the patient status table to reflect the location of the patient, e.g., the patient is in a medical exam in exam room 1.

Personnel in the hospital can check on the status of patients occupied in the exam room. FIG. 3 illustrates a screen diagram indicating a window for checking the status of an exam room. To bring-up this screen, a user can double click on the patient's name in the reception screen displayed by a client computer. As shown in FIG. 3, the Exam Room Status screen 300 is a graphical window divided into two primary sections: a banner 302 showing patient information; and a window 304 showing exam room status information. The banner 302 includes the client name, patient name, gender, weight, and species. The banner is also color coded so that the provider team can readily identify key information about the patient or client. Gender is depicted with colors (e.g., blue for male, and pink for female). A client with an overdue bill is depicted with a red colored banner (a client in "collection").

The window 304 includes a box 306 called "Presenting Complaint" that lists the service category, service description, and any further description. The window 304 also includes dynamically updated information such as the time of check-in 310 and elapsed time in the office 312.

This window also illustrates an example of how the system navigates a patient and client through an office visit. A user can change the status of a patient in the exam room by clicking on a control button 320 in the window. For example, in this screen, the user can indicate that the patient is ready for check out. This sends a message to the server, which updates the status of the patient. The reception screen can then be used to check out the patient.

The Physical Examination

When the nurse logs onto the computer located within the exam room, the physical examination for the patient assigned to the exam room is presented. No action is required on the part of the nurse to select the exam; the exam room, or the patient. The client computer in the exam room displays the Physical Examination Screen, populated with information about the patient that is checked into the exam room.

FIG. 4 shows an example of the Physical Examination Screen 400. This screen includes the following graphical elements: the client patient banner 402, the presenting complaint box 404, a preventative care box 406, a tentative diagnosis box 408, a series of buttons 410 that list and navigate to screens used to obtain input and guide the user through the physical exam, and control buttons 412–416 for changing the status of the exam.

The banner 402 and the presenting complaint box are the same features as shown in FIG. 3.

The preventative care box 406 lists preventative care services and their status in a color coded fashion. When a client signs up for a wellness plan for his or her pet, the system loads additional software components that are used to administer the plan. This is an example of such a feature. In this case, the physical exam screens display additional information about the status of the preventative care services provided under the plan. The physical exam screen prompt the user about the status of a preventative care service and tell the user when the service should be provided.

In this version of the software, the preventative care status is displayed in a color coded fashion. The possible status includes: Red=due now, Yellow=due soon, Blue=ordered this visit, White=don't give, and Green=current. This status information is dynamically updated on the server as a member of a provider team enters input indicating that a service has been performed. In addition, the system has a scheduler that determines when changes in status occur based on the order date and the current date. When the physical examination process is initiated, the server looks up the status of each preventive care item so that the most recent information can be returned to the client for display. This status information is maintained in an Accounting Sales Line Item table on the server.

The tentative diagnosis box provides the diagnosis history of the patient. This box lists diagnosis that have been made as result of previous physical exams. The diagnosis software is explained in further detail below. However, to summarize briefly, the server generates tentative diagnosis based on observations collected during the physical exam. When the doctor selects a diagnosis using the diagnosis tools, the server adds these to a diagnosis table. The server generates the diagnosis history from this table. From this window, the provider can retrieve more detailed medical history data, including diagnoses.

The physical exam buttons represent the top level in a hierarchy of physical exam screens. The physical exam is broken into the following areas:
1) Overall Condition
2) Coat and Skin
3) Ocular
4) Otic
5) Oral/Nasal
6) Respiratory
7) Cardiovascular
8) Abdominal
9) Urogenital
10) Perineal
11) Musculoskeletal
11) Neurological
12) Behavioral When the user clicks on any of these buttons, the system launches a new screen for the selected part of the physical exam. The interactive exam screens guide the user through the physical exam. As user enters information (by clicking on buttons or entering text), the server dynamically updates the database and evaluates the data to determine whether to prompt the user for additional information by displaying questions and supplemental screens that prompt the user to input medical observations.

During an initial exam, many of the observations listed in the exam screens default to normal. If an abnormal observation is checked, subsequent exams will default to the previous findings by displaying the abnormal observation as marked in a previous exam. In some instances where critical information is necessary, the user will not be allowed to exit from a screen until certain observations are made, as reflected by the user entering some observation.

Some observations trigger actions that need to be performed right away, and others trigger actions that can be performed later. In either case, the client monitors for this type of input, and when it detects the observation, it evaluates preprogrammed expressions to determine which actions should be performed right away or performed later. For actions that should be performed right away, it displays additional queries using message boxes or additional screens. As observations are made during the physical exam, the need to present additional screens is maintained in memory variables which control the operation and behavior of the exam as a whole, and the operation and behavior of individual sub-exam screens.

The user can proceed through the physical exam portions in any order, but must complete all parts of the exam before any diagnosis is performed. To reflect parts of the exam that are complete, the physical exam screen shown in FIG. 4 includes a status box (e.g., 420) next to each navigational button that links to the portions of the physical exam. These boxes are color coded to indicate the status of the corresponding part of the exam. In this version, green means all findings are normal in this part of the exam, red means that the nurse has marked abnormal findings for the doctor's review, and blue means that text questions were not answered by the doctor.

The control buttons across the bottom enable the user to control the status of the exam. For example, the user can choose to check out of the exam, to suspend the exam, indicate that the exam is complete.

Example Exam Screens

FIG. 5 illustrates an example of a physical exam screen used to record information about a patient's overall condition. The Overall Condition Screen 500 includes the banner 502, a control bar 504 across the bottom, and a variety of graphical user interface controls for collecting input (text or cursor control device) and for displaying output (including numerical data, observations recorded as text, and graphical data generated by the server).

The graphical user interface controls prompt the user to enter information because they display an item to be observed and then give the user an option to make some observation for that item. For example, in this screen, the user can select the overall condition or temperature observation by checking a check button (e.g., 510, 512). The user can enter numerical data such as temperature via a graphical box 514 that allows the user to scroll through a range of numbers. In addition, the user can enter or select text input from drop-down boxes (e.g., 516).

The screens display patient data dynamically as well. For example the temperature history box 520 displays temperature observations. The user can also choose to display a graph of the temperature by clicking on the "graph temperature" button 522.

The system also documents when services have been offered and declined by the client. For example, the screen in FIG. 5 has a box 530 entitled "Recommended Care Declined" which lists any services that the client has declined in the past.

The data displayed in this and other exam screens is dynamic in that it is updated by the server soon after it is entered. Thus, the screens reflect up-to-the-minute data, some of which may have been entered just moments ago on the same or a different client computer. The interface screens are formatted to display information about a patient, and the system draws this information from the patient's records, which are updated each time new information is entered at any client computer. When the user selects a screen for display, the patient data in the display is drawn from the current patient records on the server.

When the user initiates the exam, the server evaluates the observations and determines which questions and warnings should be displayed to the user. As the user accesses screens in the exam, these warnings or questions form part of the display screen. Thus, the display changes based on prior recorded observations.

The Control Bar

Several of the physical exam screens have a control bar such as the one shown in FIG. 5. This control bar includes graphical control buttons that provide helpful functions during the exam. The example shown in FIG. 5 includes a check mark 540, a stop button 542, an exclamation point 544, a drop down list of videos 546, a warning bell 548, and a medical note pad editor 550.

The check mark is a navigational control that enables the user to tell the server that the user is ready to move on to the next screen. The stop button halts the exam and returns the client to the physical exam screen. The exclamation point enables a nurse to check a part of the exam to call it to the doctors attention. This input event tells the doctor that he or she needs to check this part of the exam. The screen is marked in blue to tell the doctor to observe more closely.

The video screen drop down list enables the user to select and instruct the server to play a selected video. The server selects these videos dynamically based on the current screen being displayed.

The warning bell button enables a member of the team to call for help in case of a problem. When a user presses this button, the client sends a message to the server that an alarm should be played on the other client computers. In this implementation, the alarm includes a visual alert screen and an audio alert generated on the other computers within the system. An alternative is to sound an audio alarm on the other computers. The alert is triggered through the addition of a record onto the message queue that all computers in the system are monitoring. The alert is cleared through the deletion of the record.

Finally, the notepad button launches a text editor in a window that enables the user to enter a medical note. The server records the date, time, the text entered by the user, and who made the observation.

Linking of Screens

As a user makes observations, the system evaluates whether the observations require supplemental information. Some observations can generate warnings in screens for other parts of the exam. To improve performance, the client maintains the patient's exam file in memory and issues context sensitive additional questions that are generated based on observations entered during the exam. As observations are made during the physical exam, the client executing the physical exam software determines when to present additional screens. The conditions that need to be satisfied to trigger additional exam screens are maintained in memory variables which control the operation and behavior of the exam as a whole, and the operation and behavior of individual sub-exam screens.

FIG. 6 illustrates an example of a supplemental screen that is triggered in response to an abnormal observation. In this example, the client prompts the. user for more information with a supplemental screen because the user has entered an abnormal observation on the abdominal screen. The supplemental screen shown in FIG. 6 prompts the user to record any additional abnormalities from a predetermined list.

In addition to generating new questions and supplemental screens dynamically, another feature is the ability to launch other software processes in the system in response to an observation or a request to perform some treatment, For instance, if the doctor decides to prescribe a drug that is listed on a treatment list, the doctor can select that treatment by clicking on it. The client software will then launch a prescription screen so that the doctor can immediately fill the prescription. When the doctor completes the prescription and exits the prescription screen, the client sends a print job to the prescription printer. It then prints the label on the attached printer.

During the examination, the doctor may prescribe and dispense various treatments via additional user interface screens. One such screen, called the therapy screen, can be accessed via a drop down menu. As explained further below, this screen lists therapy service items that have been prescribed based on a previous diagnosis. When the doctor completes the service, he or she enters the change in status through the therapy screen. The server automatically adds service items completed during the visit to the client's invoice. The doctor can also use another screen, called the order screen, to prescribe and dispense a treatment item.

Graphical Displays Used to Enter Patient Observations

Figure 7:
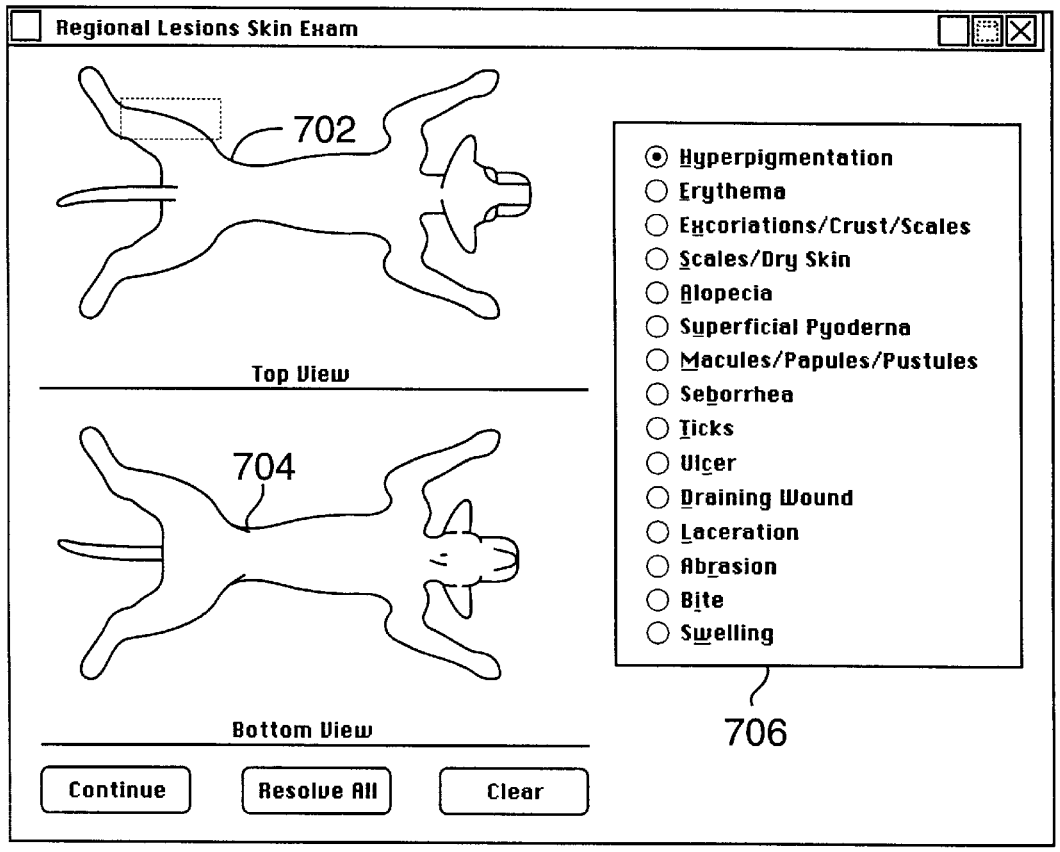
FIG. 7 is an example of an interactive user interface screen used to prompt the user for graphical input of medical observations using a graphical depiction of a patient's anatomy.

FIG. 7 is an example of a screen 700 used to prompt the user for graphical input of medical observations. In this example, the screen displays a graphical representation of the pet 702, 704 and enables the user to mark the location of lesions on the skin graphically. The graphical representation shows a part of the anatomy of the pet and is responsive to cursor input from a pointing devices such as a mouse, track ball, or touch screen. The user can mark the location of lesions on the patient using the cursor control device.

The type of observation (i.e. the type of lesion in this example) is entered via a selection list 706. First, the user selects the type of lesion by clicking on a selection in the list, and then marks the location of a lesion by positioning the cursor over the position on the graphical depiction of the skin where the lesion is located on the pet.

Each time the user clicks on the graphical representation, the client software records medical observations as observation records in a database file. These records include: the type of observation, top or bottom view, the date and time, the doctor-nurse team who recorded the observation, and the coordinates of the pixel where the user marked the lesion. These coordinates are mapped to actual bodily region (based on their location, e.g., pixel at (5, 19) is mapped to the dorsal paw).

Verification of the Exam

Figure 8:
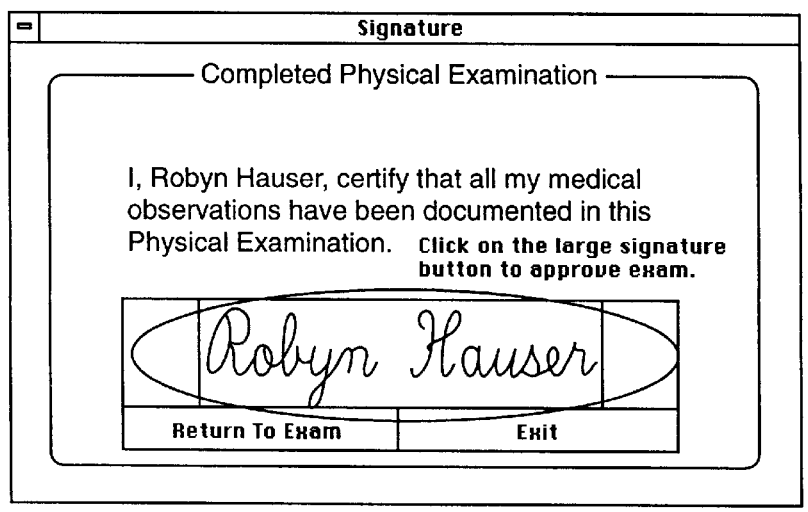
FIG. 8 is an example of a graphical display depicting the doctor's signature to prompt the doctor to verify medical observations entered into the system.

The physical exam software provides a user interface control that enables the doctor to record an event certifying that all of the observations have been documented. Specifically, the client software displays the dialog box shown in FIG. 8. The client software displays this dialog box in response to a user clicking on the exam complete button in the physical exam screen.

In order to complete an exam, the doctor must login to the system. After logging in, the doctor can review and edit the observations made by the nurse, perform treatment, etc. When complete, the doctor clicks on the exam complete button, which causes the client to display the signature box. The doctor's signature is stored as an image in the hospital database. The server ensures that the signature is inserted on all of the forms requiring a doctor's signature.

Diagnosis and Therapy Selection

Figure 9:
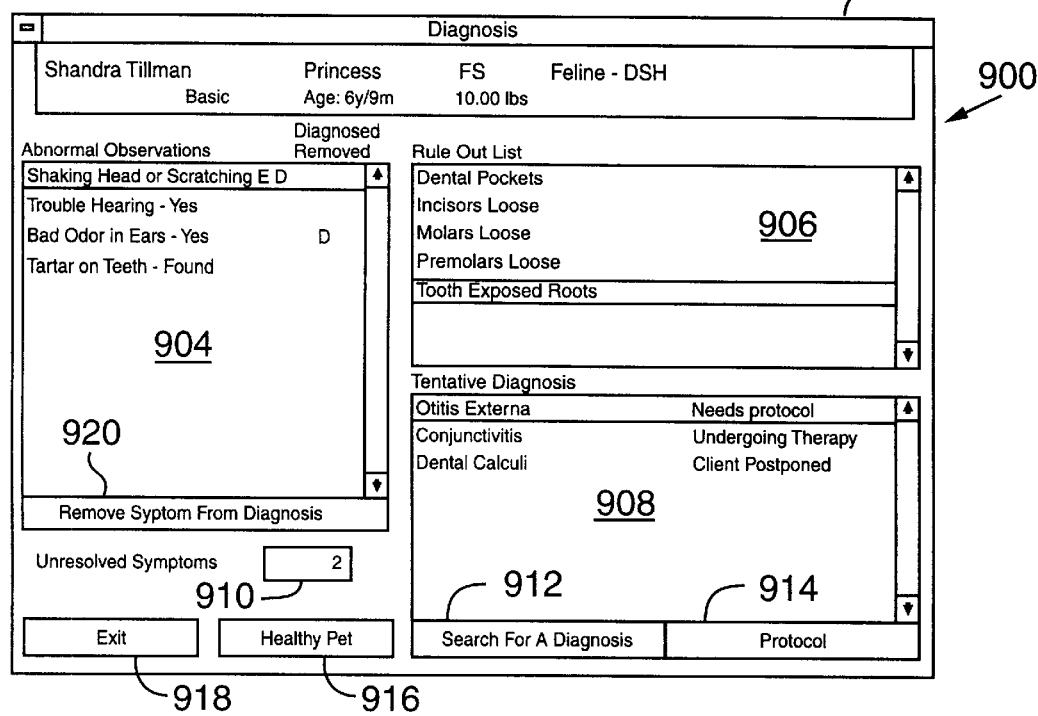
FIG. 9 illustrates an example of an interactive user interface screen used to display diagnosis generated by the system and to guide the user in selecting a tentative diagnosis.

When the physical exam is complete, the doctor can proceed to a diagnosis screen. FIG. 9 illustrates an example of the diagnosis screen. This screen is displayed in response to the doctor certifying that the exam is complete as explained above. The diagnosis screen includes the patient banner 902, a box for displaying abnormal observations 904, a box for displaying a rule out list 906, and a box for displaying tentative diagnosis 908. The box 910 labeled as "unresolved symptoms" keeps a running total of symptoms that are not linked to a diagnosis.

The diagnosis screen also includes a number of navigational controls used to navigate to other parts of the system or to launch other features. These controls include: 1) a "search for diagnosis" button 912 that launches the interface to a database search tool for keyword searching the system's list of diagnosis, 2) a "protocol" button 914 which launches a service for applying a protocol to the patient given the tentative diagnosis selected in the diagnosis screen, 3) a healthy pet button 916 which enables the team member to indicate that no diagnosis or treatment protocol need be selected, and 4) an exit button 918 used to exit the diagnosis screen and return to the main window of the client software.

When the exam is complete and certified, the client software on the exam PC sends a message to the server, which compiles a list of the abnormal observations in response and places them in a table. These abnormal observations are then displayed in the abnormal observation box 904. Each of the records in this list can be marked as either diagnosed or removed. To remove an observation, the doctor clicks on the "remove symptom" button 920. This button toggles between "remove symptom" and "use symptom in diagnosis" to enable the user to add a symptom back onto the list of abnormal observations.

The rule out list is a list of possible diagnosis automatically generated by the server. The rule out list is generated from a table that keeps a list of all ailments called the "all ailments table." Each item within the all ailments table has observations potentially associated with it. The actual observations made during the physical examination are matched against the list of observations associated with ailments. Ailments which match are then added to the diagnosis rule out list.

The doctor can select a diagnosis by clicking on an item in the rule out list. When the doctor does so, the client sends a message to the server indicating the selected diagnosis. The server removes the diagnosis from the rule out list, adds it to the tentative diagnosis, and determines which abnormal observations are linked to the diagnosis. It then marks the abnormal observations that are linked to the selected diagnosis with a "D." The server sends the results of these operations back to the client to update the display dynamically. In the display, the selected diagnosis moves to the tentative diagnosis box, the abnormal observations linked to the selected diagnosis are marked with a "D" and the unresolved symptoms count is updated to a number reflecting the number of abnormal observations that are undiagnosed aid not marked as removed.

In the tentative diagnosis box, the client also displays the status of the diagnosis, as reflected in the diagnosis table maintained on the server. The possible status includes: Needs protocol, Undergoing Therapy, Client Postponed, and Client Declined. This status is updated automatically as the user takes actions that change the status of a diagnosis. For example in this version, the initial status of a selected diagnosis is "Needs Protocol." When the doctor places the cursor over a diagnosis in the tentative diagnosis box, it becomes highlighted. The doctor can then launch a protocol by clicking on the protocol button. In response, the client sends a message to the server, which changes the status of the diagnosis to Undergoing therapy. In addition, the server generates the protocol.

To generate a protocol, the server looks up the protocol in a protocol table using the selected diagnosis as a key. The protocol for a tentative diagnosis includes one or more (typically several) recommended therapy items, each having a status. When the user clicks on the protocol button, the server generates the protocol and sends the protocol items and status to the client. In turn, the client displays a diagnostic protocol screen.

Figure 10:
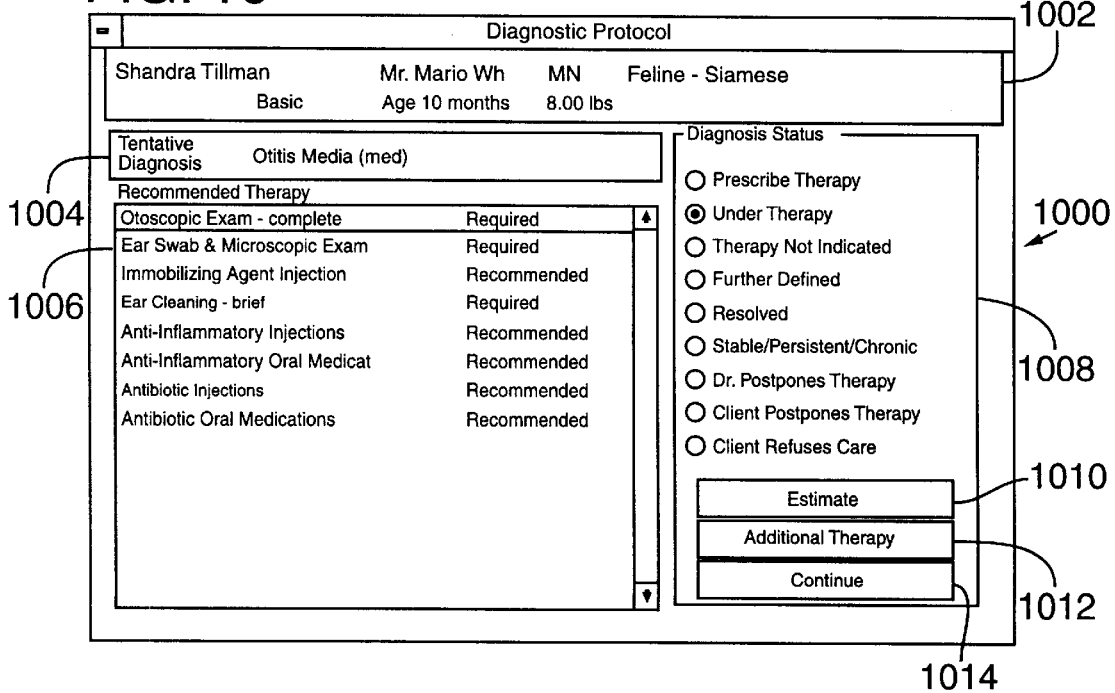
FIG. 10 is an example of the diagnostic protocol screen used to manage a treatment protocol.

FIG. 10 is an example of the diagnostic protocol screen used to manage a treatment protocol. The diagnostic protocol screen 1000 includes the patient banner 1002 (the same as in other screens described above), a tentative diagnosis box 1004, a recommended therapy box 1006, a diagnosis status check list 1008, and navigational control buttons 1010–1014 to link to other screens and launch other features.

The tentative diagnosis box 1004 lists the selected diagnosis from the diagnosis screen. The recommended therapy box 1006 lists the therapy items for the treatment protocol corresponding to the selected diagnosis. Note that the therapy items each have a status associated with them, either required or recommended. The doctor can change the status from recommended to required or vice-versa by clicking on a therapy item.

The diagnostic status check list 1008 includes a series of check buttons that enables the user to record the status of the treatment protocol for the selected diagnosis. This feature facilitates thorough record keeping and enables the medical practice to document that the protocol options were presented to the client and whether the client refused the treatment.

The navigational controls link to other screens and provide access to additional functions. One function is the estimate function, which causes the system to display a list of services, the status of the services, and a cost estimate. To access this function, the user clicks on the Estimate button. The estimate screen is described in further detail below.

The additional therapy button 1012 and continue button 1014 link to other screens. This enables the doctor to go to another screen to modify the therapy protocol.

The server compiles the services in the treatment protocol into a cost estimate. In addition, it forces follow-up in two important ways. First, it handles scheduling of the next visits and schedules follow-up calls. Second, it automatically adds prompting messages in future physical exam sessions to remind the provider team that certain observations are made and therapy service items are performed.

FIG. 11 is an example of the Estimate screen 1100. This screen can be accessed from several different screens in the physical exam and diagnostic software to show a cost estimate of product and service items that have been or are to be provided to the patient. Specifically, the cost estimated can be generated as service items are requested by the client during a visit or at the end of the visit. The Estimate screen is linked to the treatment protocol screen to give the client a cost estimate of all of the therapy service items that are to-be provided under the protocol.

The list of service items in the cost estimate is dynamically generated during patient visits, either as a result of the provider team selecting a product or service for the patient or the treatment protocol automatically adding therapy items to the list. In addition, if the patient is on a wellness plan, preventative care services are automatically added to this list when the plan is initiated. As items are prescribed for the patient, records are added to a table called the Accounting Sales Line Item table. Items added have an initial status code which indicates that the item is to be done. Once an item is completed, the status code is changed to reflect that the item is done. The status of each record reflects its status as an item which has been completed, or needs to be done. To generate a cost estimate, the server searches the Accounting Sales Line Item table in the status field to identify items that are completed and generates a list of completed items along with the cost of each item.

The Estimate screen 1100 includes the patient banner 1102, a service item box 1104, and several cost summary boxes 1106–1110. The screen also includes control buttons 1112, 1114 to print out a cost estimate and exit the screen. The services box 1104 lists the following records: a service item, its estimated cost, the name of the patient, and date completed.

The Estimate Screen estimates costs in three different categories: the wellness plan cost estimate 1106, the regular fee estimate 1108 and the client's estimate 1110.

The user can print an estimate by clicking on the print control button 1112. When the user exits the estimate screen, the client software returns to the physical exam screen. At this point, the doctor can proceed to provide the therapy for the patient. To generate the therapy screen for the patient, the user selects Therapy: patient from a drop down menu.

FIG. 12 is an example of the therapy screen 1200 used to manage the administration of a therapy service item. The therapy screen displays all the items that have been prescribed to be administered to the patient. Additional information relating to dosage is also included. The therapy screen may optionally view the current medical record from a standpoint of all items prescribed, or only those items remaining to be performed. The therapy screen allows access to other screens such as the physical examination, the medical notes, diagnosis and ordering screens, via drop down menus, navigational controls, and user selection of therapy service items displayed on the screen. The therapy screen is accessible from other screens as well via a drop down menu and navigational control buttons.

The therapy screen 1200 includes a banner 1202, a box 1204 showing therapy service items and related attributes, a list of check buttons 1206 for selecting portions of the service table for viewing, a status control button 1208 for changing the status of selected service items; a print label button 1210 for printing labels, and a remove item button 1212 for removing selected therapy service items. This screen also includes a box 1214 for viewing the tentative diagnoses, including a list of diagnoses where each diagnoses has a date and status attribute. Finally, the therapy screen includes navigational buttons 1220–1226 used to link to other screens and access other functionality.

The box of therapy items 1204, in this version, includes a list of product and service items, with fields for the date the order was received, the quantity of the item, and the status. In the case of prescriptions, the box also displays dosage and frequency. This box 1204 enables the doctor to view a list of service items scheduled for a patient to keep track of what has been done and what needs to be done. When the doctor or other member of a provider team provides a product or service, the team member can update the status of a service item in the patient's data by selecting an item and indicating that it is done. For instance, the doctor can select items and press the "make all done" button to indicate that the status of these items has changed from "to-do" to "done." In response, the server dynamically updates the status of the data in the patient's database. The client sends a message to the server with the change in status so that the server data matches the status currently displayed on the screen of the client computer. In a similar fashion, the doctor can remove items from the list by selecting them and clicking on the "remove items" button 1212.

The print labels button is used to initiate a print process for printing a label for a prescription selected from the list of items in the list of therapy box 1204. When the user clicks on the print labels button 1210, the client sends a message to the server with the pertinent data about the prescription. The pharmacy computer then retrieves this message from the server and processes the request by initiating a print process to print a label with the information provided in the message.

The navigational buttons 1220-1226 link to other screens. For example, the physical exam button 1222 links to the physical exam screen.

Client Check Out

Figure 13:
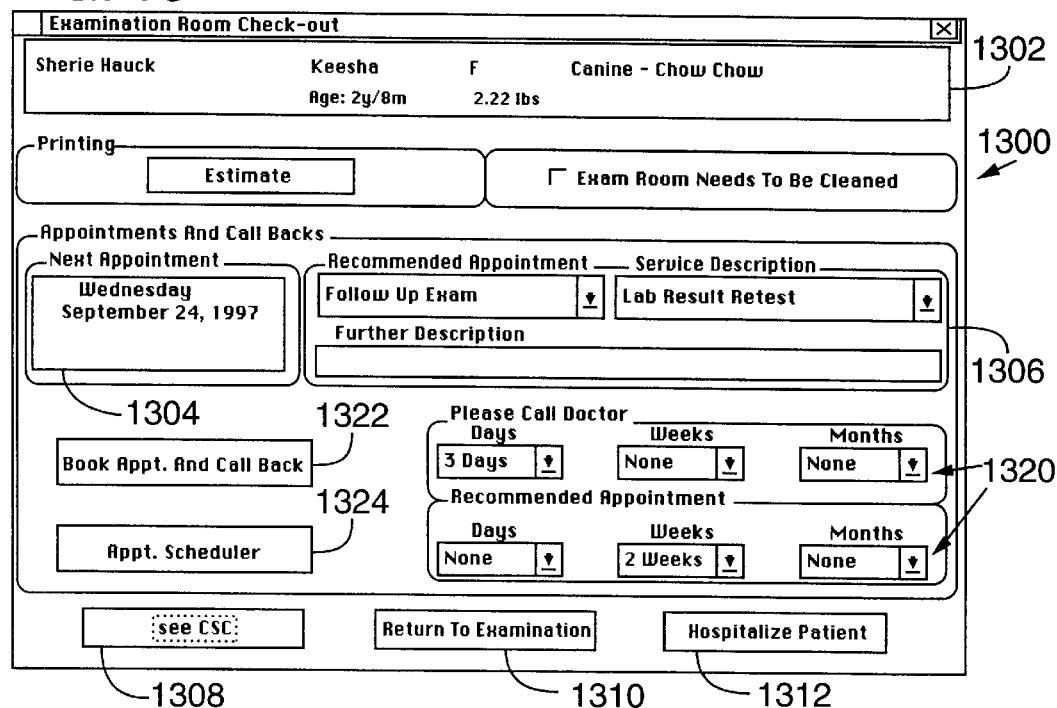
FIG. 13 is an example of an interactive user interface screen used to check a patient out of an exam room.

To complete a patient visit and transfer a patient's file to checking-out status, the doctor (or other member of the provider team) returns to the physical exam screen (FIG. 4) and then selects the Exam check-out button 402. This causes the client computer to display an exam room check out screen. An example of this window is shown in FIG. 13.

The exam room check out screen includes a patient banner 1302, a "next appointment" message box 1304, a service message box 1306, and control buttons 1308–1312, 1322–1324. The "next appointment" message box displays the next appointment scheduled for the patient from the patient's medical record stored on the server. The service message box 1306 is used to display and enter a service category, service description, and any additional descriptive information about a service item to be provided at an appointment. The user enters this information by selecting it from a predetermined list or entering it via the keyboard.

The exam room check out window includes a number of list boxes 1320 displaying "Days", "Weeks", and "Months" that enable the user to select an approximate time for a call-back or another appointment. When the user enters information in these boxes, the button 1322 shown as "Book Appt. And Callback" changes from "No Appt. Or Callback" to "Book Appt. And Callback" to reflect that an appointment is being scheduled.

After entering information for an appointment and/or callback, the user can click on the button labeled 1322 to cause the server to schedule the appointment or callback. The server has a scheduler program that can schedule appointments based on load (attempt to schedule appointments off-peak time periods). If the user requests an appointment by clicking on button 1322, a scheduler on the server will search for a time slot available near the approximate time entered by the user and enter a record of the appointment for the available time. For call backs, the scheduler will schedule a reminder for the provider team to call the client back at or before the approximate callback time entered by the user. If the user wants to view the available time slots and schedule an appointment directly, he or she can launch the user interface for the scheduler by clicking on the appointment scheduler button 1324. This brings the user to another screen used for the scheduler.

The "return to examination" button 1310 is a navigational control that allows the user to return to the main medical exam screen shown in FIG. 4. The "hospitalize patient" button is used to navigate to another screen to check the patient into the hospital and change the status of the patient to "hospitalized."

From the exam room check out screen 1300, the user can also issue an instruction to print an invoice of all the chargeable items provided during the visit. As products and services are provided during the visit, the provider team enters them. The server updates the status attributes in the patient's data base and also keeps a running list of the chargeable items in a separate invoice table. When a user instructs the client to print an invoice, the client computer sends a message to the server, which in turn, initiates a print process on the receptionist computer. The invoice is then printed at the printer in the receptionist area.

Once the user enters an appointment or notes that no appointment is necessary via the button 1322, the "See CSC" button 1308 becomes active (CSC means Customer Service Consultant). This button allows the user to navigate to the "Reception" screen shown in FIG. 14. When the user clicks on this button 1308, the status of the patient changes to "checking-out."

Figure 14:
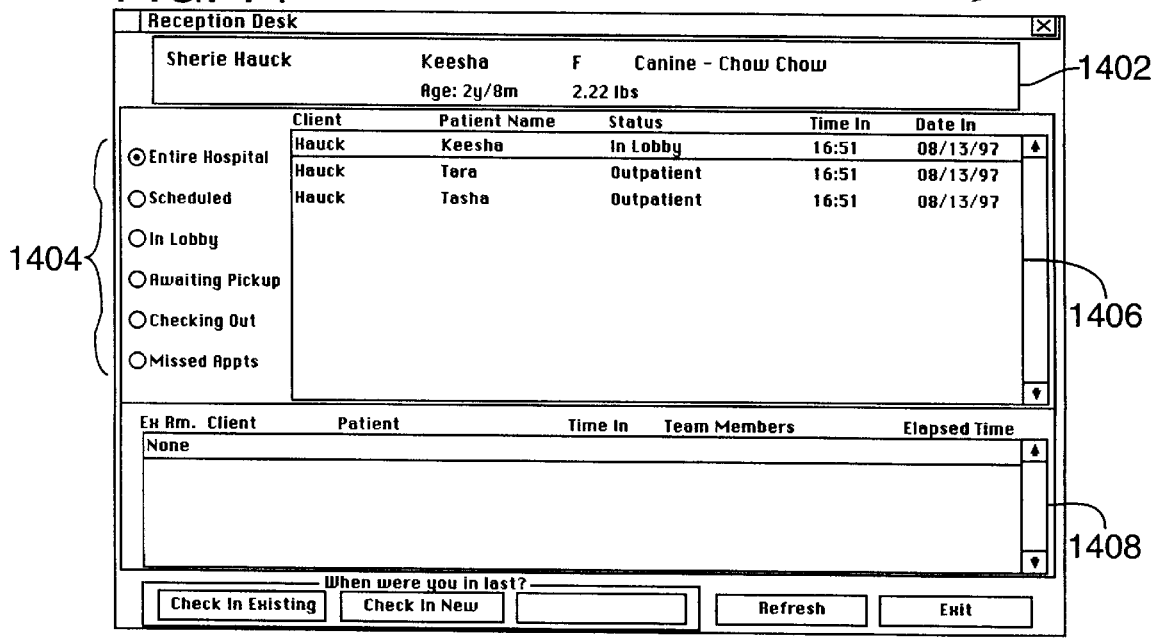
FIG. 14 is an example of an interactive user interface screen used to check patients in and out of a medical office and to monitor the status of patients in the office.

A user, typically the customer service consultant at the reception computer, checks a patient out of the facility at the reception desk screen 1400 shown in FIG. 14. This screen shows the patient's banner 1402, a list of check buttons 1404 for controlling the display, a box for viewing patient status 1406, and another box for viewing the status of the exam rooms 1408. The check buttons 1404 enable the user to control which patient status data is displayed in the box 1406. For example, if the user selects the button labeled "Entire hospital," box 1406 displays the status of patients in the entire hospital. If the user selects the button labeled "scheduled," the box 1406 only displays patients that are scheduled.

The reception screen also enables a user to check the status of patients in the medical exam rooms. The user can select (e.g., double-click on) a patient name from the lower box 1408 to display the status of the patient in an exam room, including a description of the service category (e.g., preventative care), the service description (e.g., vaccination), the time that the patient was checked into the exam room, and the elapsed time that the patient has spent in the exam room.

During the check out process, the receptionist returns any items left at the hospital, as reflected on a patient check in screen, which is accessible from a patient drop down menu at any time during operation of the system. The receptionist receives or confirms some form of payment and then checks the patient out of the hospital by selecting a check out option on the screen. When the receptionist checks the patient out, the patient's visit is over and the status of the patient is updated to reflect that the patient is checked out. At this point, the system discontinues tracking the time spent in the hospital.

Wellness Plan Software

The software for managing a health care practice described above interacts with additional software components that manage wellness plans for patients. In the following sections, we describe an implementation of wellness plan software integrated with the veterinary practice management software above. While our description is specific to wellness plans for pets, the software could be applied to wellness plans for humans as well.

Before describing the software in detail, it is useful to provide an overview of its operation. The wellness plan software enables a user to select from among two or more pre-defined wellness plans. Each of these plans has a number of product and service items associated with it. Some plans have additional options in addition to standard options that the client can select. For example, the client can select additional wellness plan optional items such as spay, neuter, hip dysplasia, etc. on puppy/kitten plans. Once the user has selected a plan and any plan options, the user is prompted for billing information used to administer the plan. The user is also asked to confirm acceptance of the plan. Upon acceptance, the software schedules patient visits and establishes a set of service or product items that the patient is entitled to under the selected plan.

During patient visits, the wellness plan software operates in conjunction with the software that guides the hospital's provider team through an office visit. The wellness plan software determines which product and service items provided to the patient are subject to a discount under the wellness plan. It also generates cost estimates of the savings provided by the wellness plan.

The wellness plan software also tracks provider team actions associated with the promotion of wellness plans. By tracking promotional efforts in this manner, the software can determine bonuses for employees as an incentive to educate clients about the plan and increase wellness plan enrollments.

The implementation of the wellness plan software includes the following principal components:

1) a wellness plan designer component running on the hospital computer system or network 2) a local wellness plan administrator component running on the hospital computer system or network; and 3) a central wellness plan administrator component running on a remote computer.

The software for the hospital computer network is designed according to a client server model. Components 1 and 2 above run on client computers and a server computer is used to maintain data and to enable resource sharing among the client computers linked to the server via the network.

This software architecture is designed to allow for central administration of wellness plans for a number of different hospitals. The central administrator software runs on the central computer and manages the wellness plans for a number of different hospitals around the country. In the current implementation, the central administrator obtains selected files from the server computers located at hospital locations. These selected files include billing information used to administer payment for the wellness plans, accounting information to generate a variety of reports to track financial information associated with the plans, and employee data used to compute bonuses for promoting the wellness plans.

The local wellness plan administrator software runs on the server and one or more other computers on the networks installed in the hospitals. One part of this software is conventional communication software that is used to dial up the central computer and transfer copies of database files associated with the wellness plans. Since the wellness plan software is integrated with the medical management software described above, there is no distinction between this communication software and the software used to transfer medical records to the central computer. Another part of the software is the software used to track and compute plan discounts and to track promotional activities of employees. These and additional features are detailed below.

The wellness plan designer component runs on the server and one or more other computers on the networks installed at the hospitals. This part of the system is used to display promotional and educational information about plans and to handle the process of setting up new wellness plan contracts. The designer also has an appointment scheduling component that is used to schedule appointments for patients under the wellness plans.

The wellness plan software is implemented as an extension to the medical management software described above. The medical management wellness plan software is a database application implemented in the FoxPro® database development environment. Though not required, most hospitals adhere to a client server model where a database client application runs on the user's computer and the database server application runs on the server computer. Like the medical management software, the wellness plan software is written in FoxPro® database developement environment for the Windows® operating system and uses native FoxPro® database file structures. To simplify the discussion, we refer to the client database software as client software and the database server application software as server software.

While a typical hospital will have a network configuration and employ software in the client-server architecture, it is also possible to implement the functions of the client and server components on a single computer in small hospitals that do not have a computer network.

Figure 15:
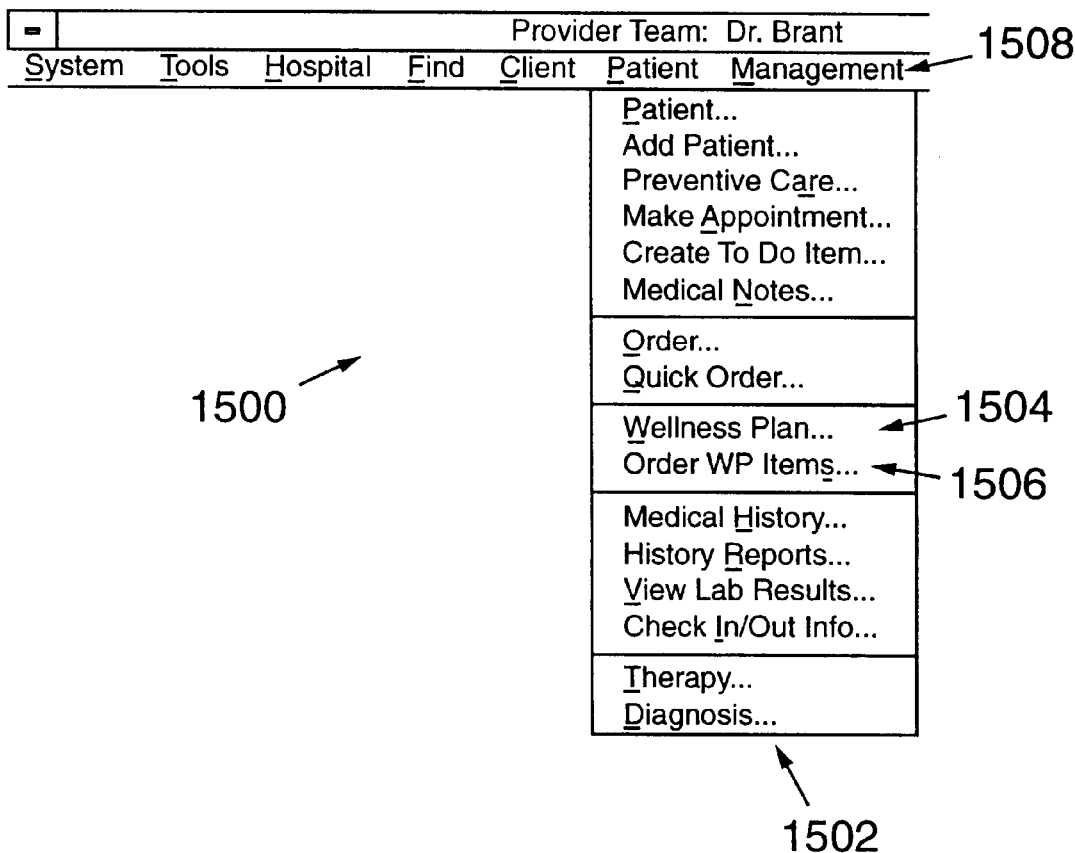
FIG. 15 is a screen diagram illustrating a menu list for invoking wellness plan software.

The wellness plan software running at a hospital network is integrated with the medical management software. FIG. 15 is a screen diagram 1500 illustrating a drop-down menu 1502 used to access wellness plan software from within the medical management software. The option listed as "Wellness Plan . . ." 1504 is used to open a screen entitled "Wellness Control Center," a user interface that educates clients about wellness plans and helps them select a plan. The option listed as "Order WP Items . . ." 1506 is used to control the use of wellness plan service or product items. Each of these features are addressed further below.

Tracking Wellness Plan Observations

The wellness plan software at a hospital tracks events associated with wellness plans in order to keep records of promotional activities of provider team members. The software records these events in two ways: 1) automatically in response to a provider action associated with a wellness plan; or 2) in response to an explicit entry of a wellness plan observation. An example of the first way of recording an event is when the user invokes "selling screens" to give a client a presentation about wellness plans. This event is recorded automatically when the user selects the wellness plan "selling screens." In this case, the event is attributed to the user that is currently logged into the client computer. An example of the second way of recording an event is in a dialog box that is designed to prompt the user for user ID information to record an observation. The dialog box can be triggered explicitly in response to an explicit request to display the dialog box or automatically when the user invokes the wellness plan software. For example, in the current implementation, a user can cause the client computer to display the dialog box by pressing a special control key (e.g., F9).

Figure 16:
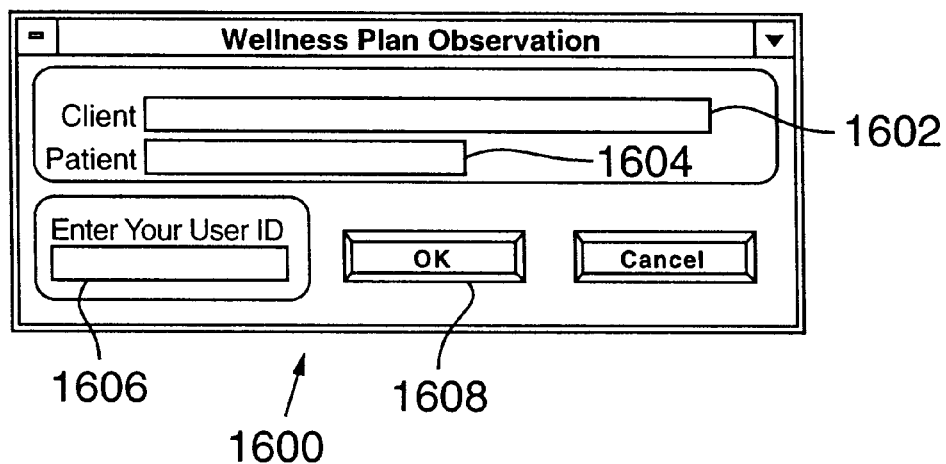
FIG. 16 is a screen diagram illustrating a dialog box used to record an event relating to the promotion of a wellness plan.

The dialog box appears automatically when a user selects the wellness plan software. For instance, when a user selects the "Wellness Plan . . ." option, the local wellness plan software running on the computer presents a dialog box to record a wellness plan observation. An example of this dialog box is shown in FIG. 16. As illustrated in FIG. 16, the dialog box 1600 includes text boxes to record the client and patient names as well as the user ID of the provider team member that is currently working with the patient (1602–1606).

When the wellness plan software captures an automatic observation or an observation entered at the dialog box, it keeps a record of the event. In response to the user clicking the OK button 1608 in the dialog box, for example, the client software running on the computer creates a data record indicating the clinic, employee ID, customer (also referred to as the client), pet, date and time. The client sends the data record to the server where it is stored as a new entry in a bonus observation table.

Selecting a Wellness Plan

Figure 17:
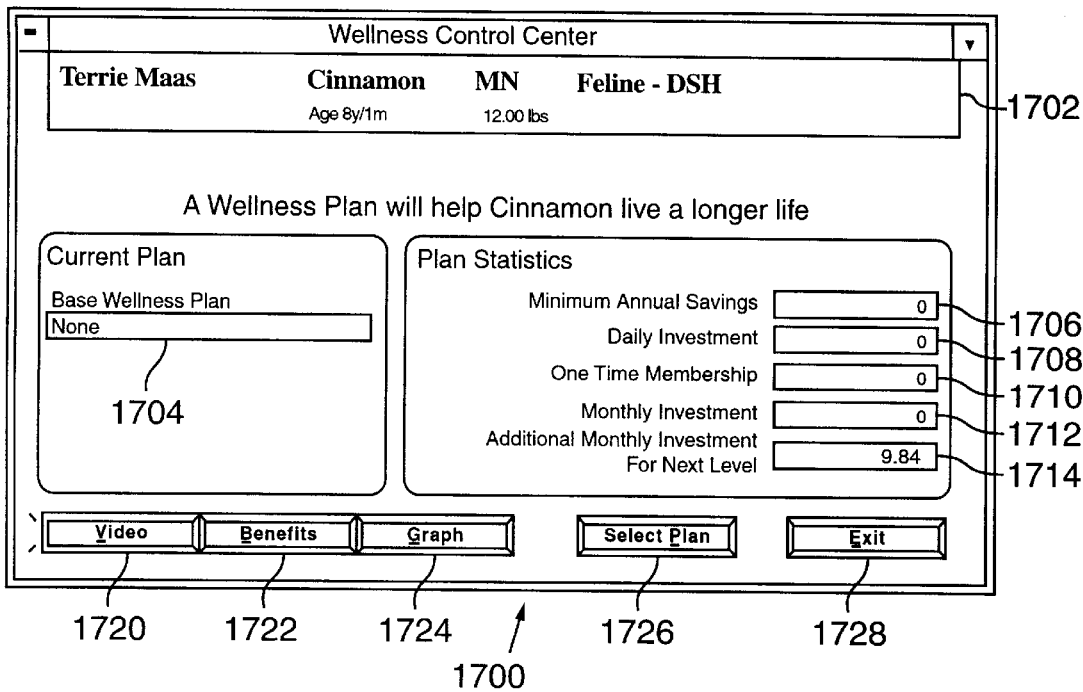
FIG. 17 is a screen diagram illustrating a Wellness Control Center window used to educate clients about wellness plans and to promote the plans.

To select a wellness plan, the user begins by selecting the "Wellness Plan . . ." option 1504 from the drop down menu of FIG. 15. After the wellness plan observation is recorded, the client displays a Wellness Control Center window as shown in FIG. 17. The control center window 1700 displays the patient banner 1702, a text box for listing the plan, a series of text boxes showing plan statistics (1706–1714), and a variety of control buttons (1720–1728). The control center window displays the minimum annual savings 1706, daily investment 1708, one time membership fee 1710, monthly investment 1712, and the additional monthly investment for the next higher plan level 1714. The identity of the current plan is obtained from a Wellness Plan Contract file for the client and patient that the user has selected. For example, in FIG. 17, the currently selected client and pet are illustrated in the patient banner 1702. This particular pet is not enrolled in a wellness plan yet, so the current plan text box 1704 displays "none."

From the control center, the user can initiate the display of educational and promotional information about wellness plans. For example, the video button 1720 invokes a program to show videos about wellness plans relevant to the pet. The benefits button 1722 cause the client software to display a series of screens that explain the benefits of wellness plans.

Figure 18:
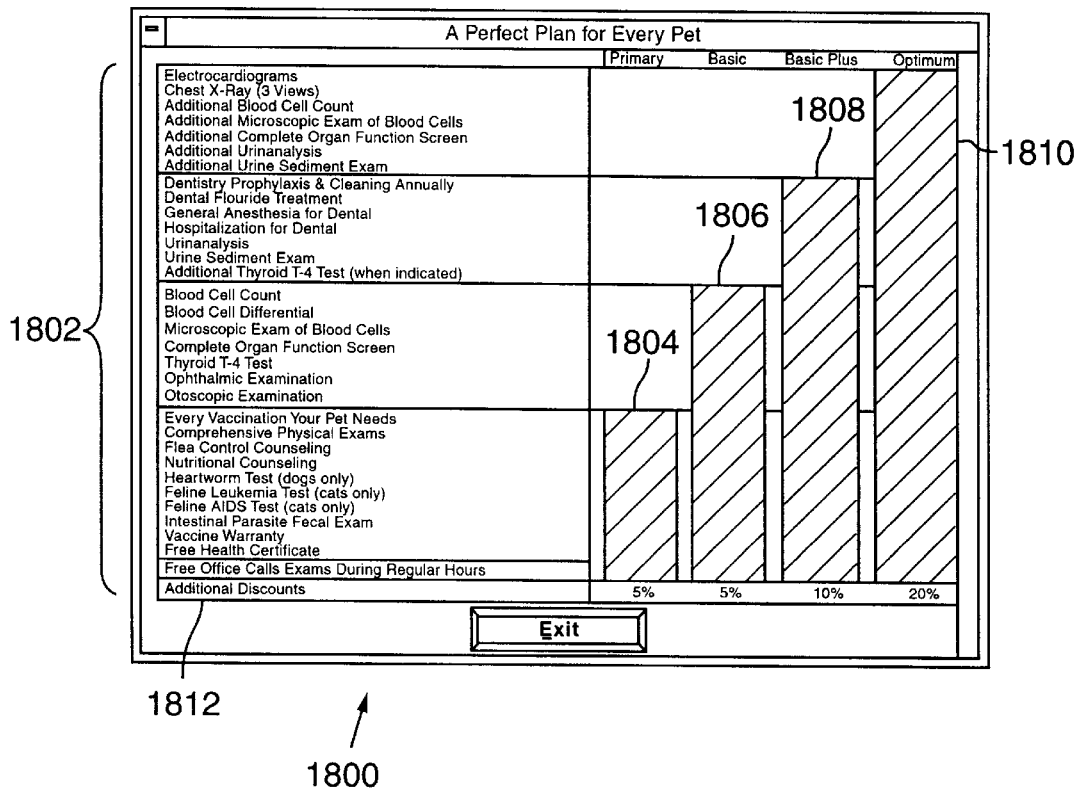
FIG. 18 is a screen diagram showing an example of a window used to depict the service items provided under a variety of different wellness plan levels.

The graph button 1724 shows a chart of the service and product items associated with different wellness plans. FIG. 18 is a screen diagram 1800 illustrating an example of this type of chart. Along the left hand column, the chart 1800 shows a list of service items 1802. Each plan has a bar graph (1804–1818) that indicates which of the product and service items are covered under the respective plans. The chart also displays the additional discounts 1812 associated with the plans.

Figure 19:
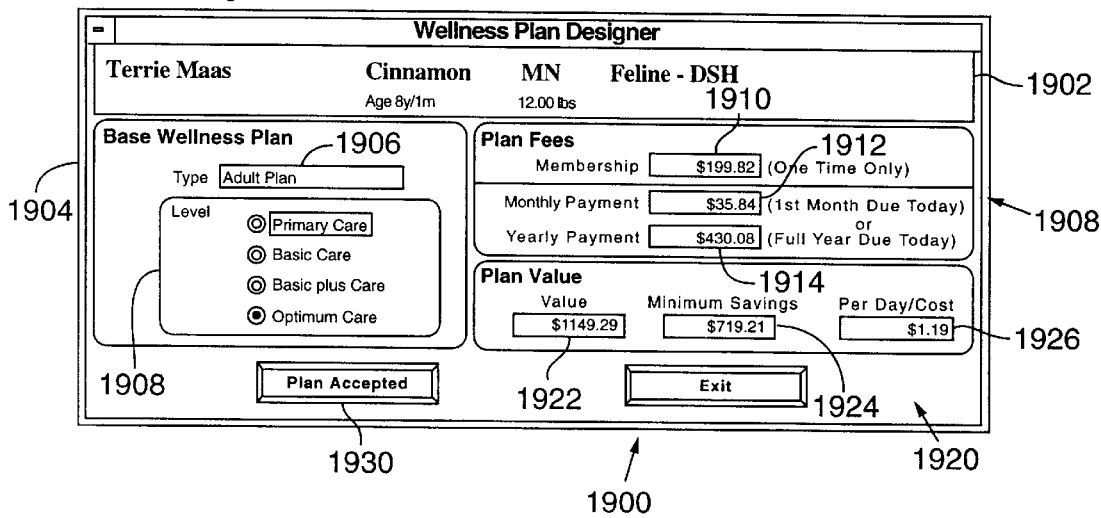
FIG. 19 is a screen diagram showing an example of a Wellness Plan Designer window used to select a wellness plan.

When the user chooses the "select plan" button 1726 from the control center window of FIG. 17, the client software displays a Wellness plan designer window. An example of this window 1900 is shown in FIG. 19. The top portion of the window 1902 shows the patient banner. The left portion 1904 of the this window shows a text box 1906 listing the type of plan and a check list 1908 for selecting the level of plan. The right portion 1908 of the window shows a number of text boxes (1910–1914) for displaying fees associated with the plan type and level. The lower right portion 1920 displays figures to indicate the plan value 1922, minimum savings under the plan 1924 and per day cost 1926. These values are assigned to the wellness plan when the plan is created at the central facility.

If the client wishes to accept the plan, the user then selects the "plan accepted" button 1930 on the lower left portion of the display. This causes the client software to add an entry in the patient's medical record indicating that the patient is on a wellness plan. In response to the user selecting the "plan accepted" button, a wellness plan contract record is created on the server that reflects the terms of the agreement, and is set as tentative until the contracting process is finalized. In this particular implementation, the process is finalized when the client signs and pays for the contract as explained below.

Figure 20:
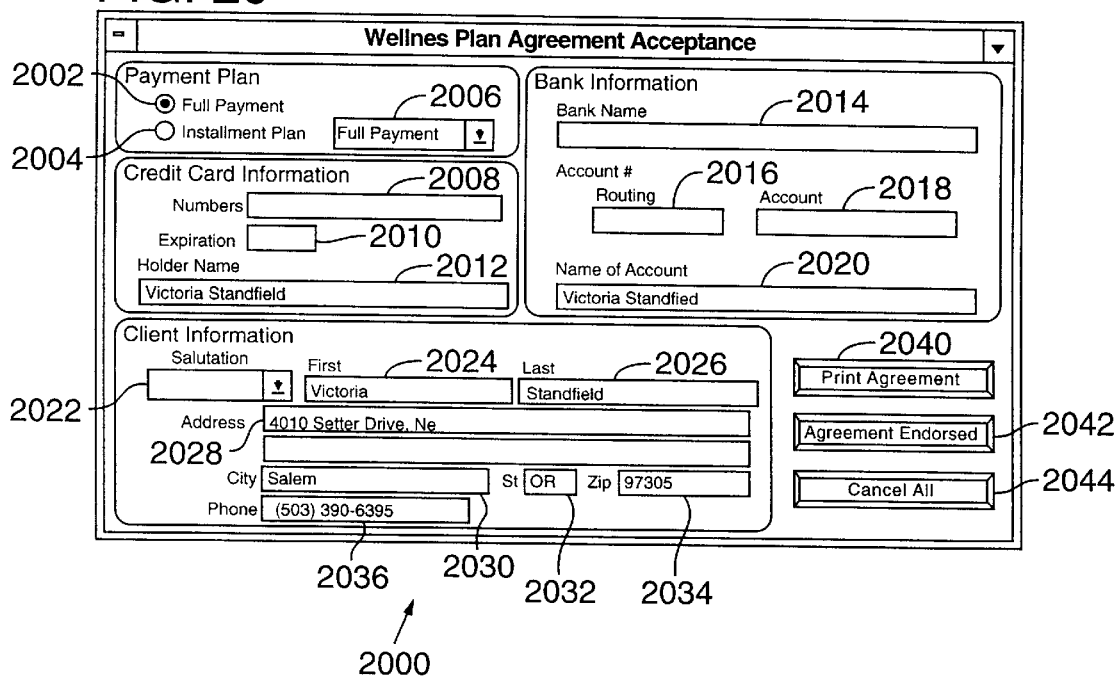
FIG. 20 is a screen diagram showing an example of an Agreement Acceptance screen used to obtain billing information from the client and to confirm that the client wishes to order a plan.

After selecting the plan via the "plan accepted" button 1930, the user then completes the plan acceptance procedure by selecting "Client to Invoice" from the client drop down menu (see FIG. 15, for an example of the drop down menu). By selecting the "Client to Invoice" option, the user causes the system to display a Wellness Plan Agreement Acceptance window. FIG. 20 illustrates an example of this window 2000. As shown in FIG. 20, the user can select a payment plan (full payment or installment plan via check buttons 2002–2004 and list box 2006), enter credit card information or bank information via text boxes 2008–2020, and enter client address information for billing purposes 2022–2036.

After entering this information, the user can then print the wellness plan contract by selecting the "Print Agreement" button 2040. Once the client has signed the agreement, the user then selects the "Agreement Endorsed" button 2042. If the client changes his/her mind, the user can cancel the agreement by selecting the "cancel all" button 2044. By selecting the cancel all button, the user causes the client software to re-compute the invoice for any product or service items for the current visit to reflect that the patient is not on a wellness plan.

When a wellness plan agreement is endorsed, the tentative contract record that has already been created is updated to reflect the payment terms and to indicate that the contract is final, as opposed to being merely tentative. The contract records are stored in a Wellness Plan Contract table on the server and include an indicator of the clinic, client, patient, level of plan, date initiated, initiation amount, number of payments, payment starting date, and payment amount. Additional items stored in a wellness plan contract record can include payment method preference, checking account bank number, checking account number, credit card number, and credit card expiration. At plan endorsement, the patient record on the server is also updated to reflect that the tentative agreement has been initiated.

When a contract is created, the client software causes the server to set-up a Wellness Plan Item table to store a list of wellness plan service and product items associated with the selected plan level and type. The server retrieves this list from a wellness plan table. The records in the Wellness Plan Item table are assigned an initial status of open/to-do and are flagged as being part of a wellness plan. These records also include the regular price for the item so that the wellness plan software can estimate cost savings for comparison during invoicing at patient visits. During a patient visit, an Accounting Sales Line Item table is established to track product and service items provided to a patient during a visit. To estimate plan discounts during a visit and compute the invoice, the accounting sales line items for the visit are matched against the wellness plan items on a case by case basis to determine whether items provided during a visit are covered by the wellness plan and whether an item has not yet been provided.

The wellness plan item table stores an un-discounted retail value with each service item in the table so that the production of a provider team member, e.g., a doctor, can be computed based on the retail value.

Once a wellness plan is created, the discounts available under the plan are available immediately. Before the wellness plan item records are created, the server examines the accounting sales line item records associated with the current visit. Wellness plan pricing and service items covered under the plan are applied to the items provided during the current visit. This may include making the office visit/ physical exam fee zero. This may also include discounting the items that were provided during the current visit, which are not specifically wellness plan service or product items. The wellness plan items applied to the current visit are not removed from the wellness plan item table made for the plan, but instead are flagged as consumed.

During a visit, the user can select wellness plan product or service items that the client wants to apply to the current visit. The drop down menu 1502 of FIG. 15 has an option called "Order WP items" 1506. When the user selects this option, the client software displays a window listing wellness plan product and service items for the current patient. Only the wellness plan items which are not flagged as consumed are displayed in this window. This list is created from the Wellness Plan Item table for the patient.

Figure 21:
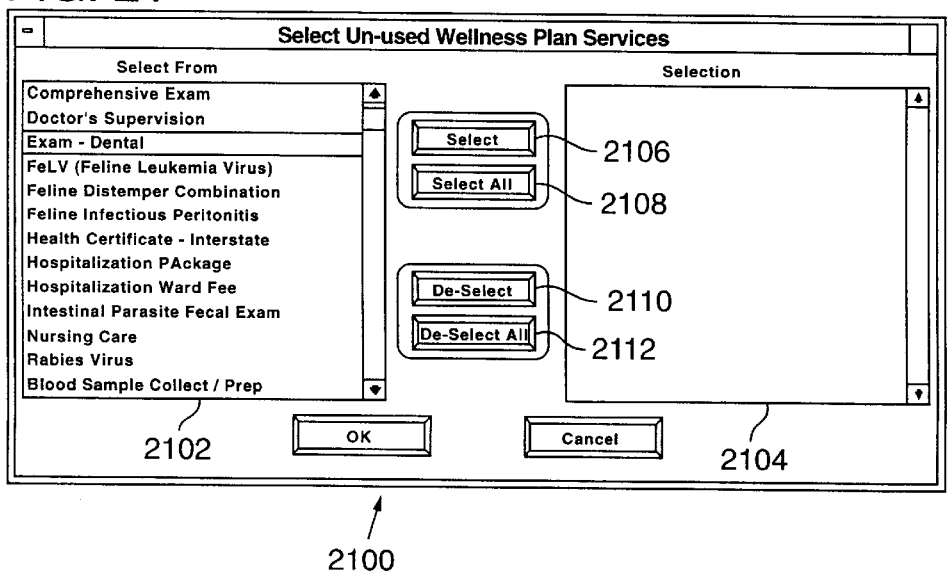
FIG. 21 is a screen diagram illustrating an example of a screen used to select specific Wellness plan items and apply them to service items provided during a current patient visit.

FIG. 21 illustrates an example of a display window 2100 that displays wellness plan items. This window includes a "select from" box 2102, listing the wellness plan product and service items to select from, and a "selection" box 2104, listing any selected items. The user selects items using the "select" and "select all" buttons 2106, 2108, and the user de-selects items using the "de-select" and "de-select all" 2110, 2112 list. Wellness plan items that have already been provided are flagged so that they are not displayed in the "select from" box 2102. When the user selects a wellness plan item and clicks "OK," the software causes accounting sales line item records to be created in an Accounting Sales Line Item table on the server for each of the wellness plan items selected.

Scheduling Office Visits

When the wellness plan contract is endorsed, the server automatically schedules preventative care appointments for the patient. In the current implementation, the server determines the number of appointments that need to be created by checking the Wellness Plan Contract table associated with the selected plan. The server creates appointment records for two appointments per year. Appointment records are stored with the patient's records and indicate the time and date of the appointment. A pre-selected list of wellness plan service items are associated with each visit. This list of items is defined in a table used to store details for each wellness plan, called the Wellness Plan Details table. The Wellness Plan Details table lists the service items associated with wellness plan visits and other plan details, such as plan pricing and a list of items covered by the plan. More information on the Wellness Plan Details table is provided below.

The provider team can re-assign wellness plan items among the scheduled visits by selecting the desired service items for a visit with the wellness plan order feature explained above and illustrated in FIG. 21.

Figure 22:
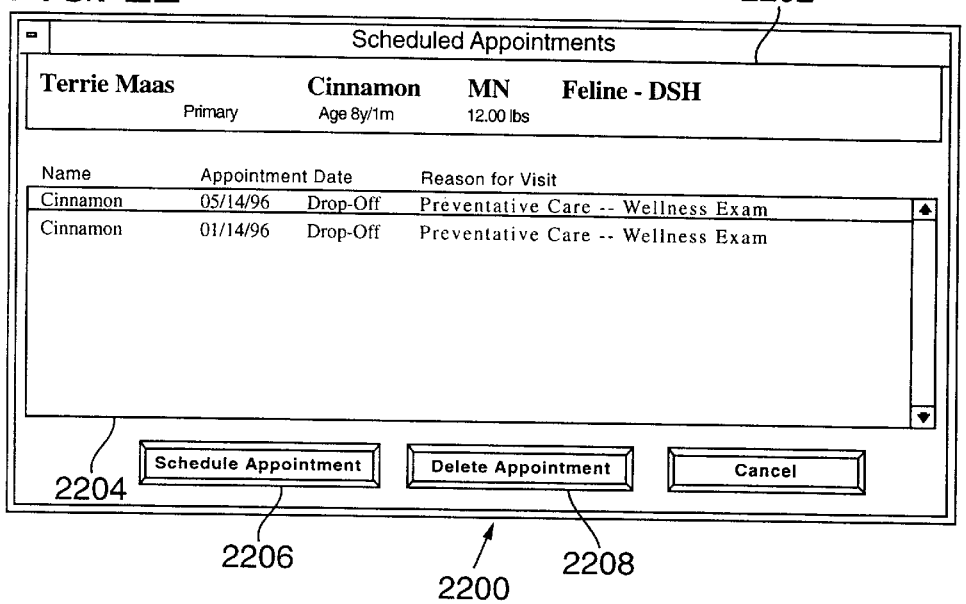
FIG. 22 is a screen diagram illustrating an example of a screen display used to show preventative care appointments scheduled for a patient.

FIG. 22 illustrates an example of a display screen 2200 showing scheduled appointments immediately after a client has endorsed a wellness plan. This window includes a patient banner 2202 for the current patient and client and a box 2204 listing scheduled appointments and several attributes associated with the scheduled appointments. For example, this window shows the patient name, date of the appointment, and reason for the visit. Note that visits scheduled under a wellness plan are referred to as preventative care.

The scheduled appointments screen 2200 includes control buttons labeled "Schedule Appointment" 2206 and "Delete Appointment" 2208. When the user selects button 2206, the software displays a scheduler window that enables the user to manually schedule an appointment. The user can delete an appointment by selecting an appointment entry displayed in the box 2204 and then selecting the delete appointment button 2208.

The software includes an auto-scheduler that automatically schedules wellness plan appointments in response to a wellness plan contract being finalized. In performing this auto-scheduling function, the software assumes that the first wellness plan appointment is the day that the contract is started. If it is not, then the first appointment is entered manually by the user via an appointment scheduler window. The user can access this window by selecting the "Make Appointment" option under the "Patient" drop down menu list shown in FIG. 15. Once the first appointment is established, the software automatically schedules the next appointment. The software is pre-programmed with peak and non-peak months. It uses the peak and non-peak month data and the date of the initial appointment to find a new time and date for the next appointment during a non-peak month. Like other plan administrator software at the medical facility, the scheduler software runs on the client computer and stores its data on the server.

Whether scheduled automatically or entered manually by the user, the appointments are stored as records in an appointment file. This file is maintained on the server, and it is also sent periodically to the central computer so that appointment data can be maintained on the central computer as well.

Patient Visits

When a client brings a patient to the hospital for a visit, the provider team uses the medical management software described above to track the patient's progress through the visit. In addition, the provider team uses the medical management software to guide it through the medical exam process. As product and service items are provided, they are recorded in an Accounting Sales Items table created for the visit. The medical management software uses information from the Wellness Plan Item table to estimate cost savings dynamically and to apply wellness plan discounts.

Estimating Cost Savings

The software can dynamically estimate cost savings attributable to a wellness plan as product and service items are selected during a visit. As an example., consider the Estimate window shown in FIG. 11. During an office visit, product and service items that are provided or are scheduled to be provided are added to the Accounting Sales Line Item table. The records in this table include information about each item, including the value under the wellness plan and the regular retail price.

As items are ordered, a member of the provider team updates the status of the item to "done," meaning that it has been provided. This action causes a new record for the item to be added to the Accounting Sales Line Item table. As items are ordered, the client software checks the Wellness Plan Item table to see if there is an un-used item corresponding to the item that has just been ordered. If there is an un-used item, it adds a record to the Accounting Sales Item table with a field indicating the appropriate cost under the wellness plan (the actual cost). If there are no un-used items corresponding to the item, it adds a record with a field snowing that the actual cost is the regular price.

Items covered under the wellness plan can be ordered in this manner or by specifically ordering wellness plan items as described above in connection with FIG. 21. The user interface of FIG. 21 is preferred because it enables the user to select from wellness plan items that are not flagged as consumed.

The software updates the cost estimates shown in FIG. 11 as the user selects product and service items. To compute the basic wellness plan estimate 1106 regular fee estimate 1108, and the client's estimate 1110, the software totals the wellness plan, regular fee and actual prices from corresponding pricing fields in the records in the Accounting Sales Item table for the current visit. Note, as an alternative, the software can also compute cost savings by summing the difference between the actual and retail price fields for each of the records in the Accounting Sales Item Table.

Applying Wellness Plan Discounts

The software computes a final invoice in a similar fashion as the cost estimates described above. Specifically, it sums the pricing information in the pricing fields of the accounting sales line item records. In addition to computing the invoice amount and wellness plan amounts, the software flags items that have been provided as being consumed, and stores a link from items in the Accounting Sales Item table to the Wellness Plan Item table. This link enables users to easily verify that wellness plan service items have been provided.

Wellness Plan Status

Figure 23:
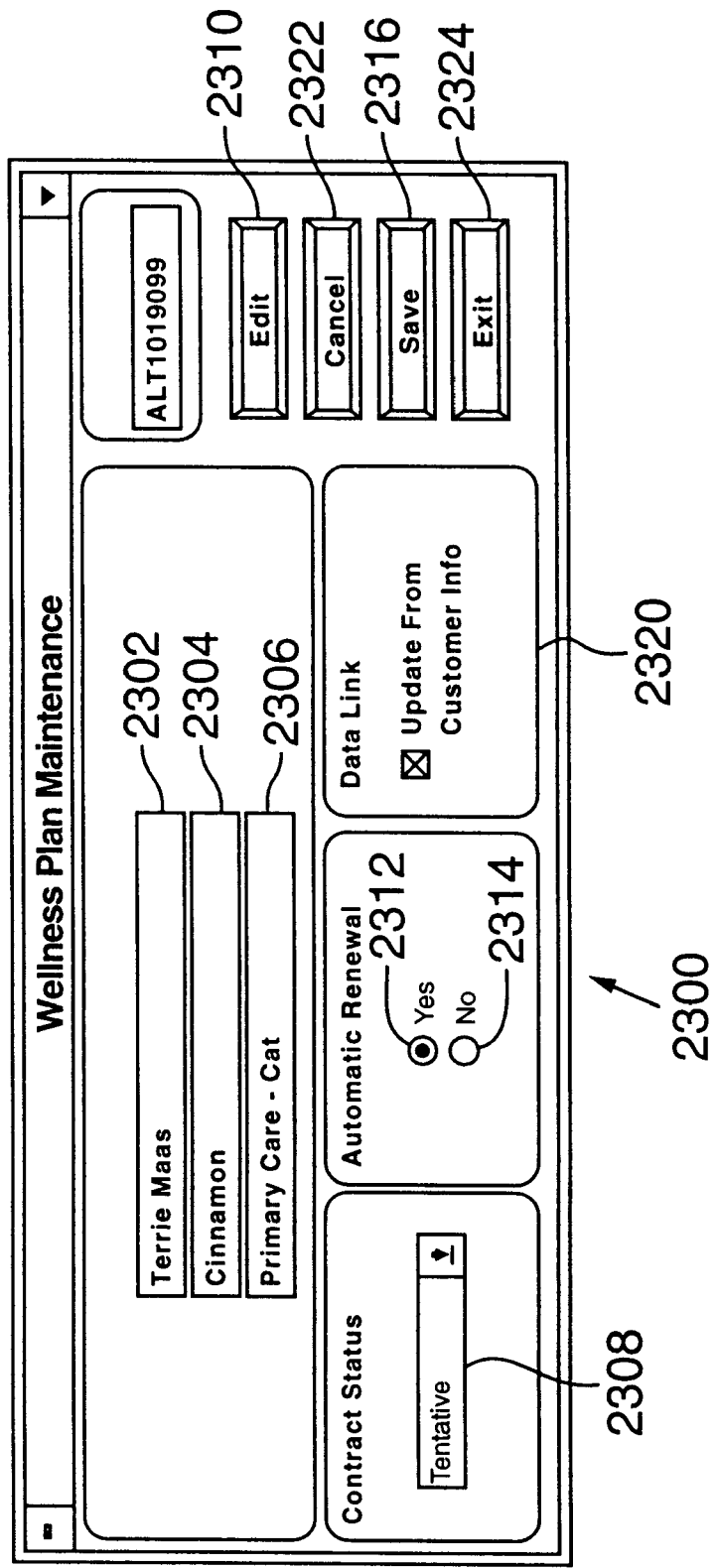
FIG. 23 is a screen diagram illustrating an example of a window used to update the status of a wellness plan.

The software provides a way for authorized users to change the status of a patient's wellness plan. From the "management" drop down menu 1508 shown in FIG. 15, an authorized user can access a Wellness Plan Maintenance display screen. An example of this screen 2300 is shown in FIG. 23. In order to access this screen, the user must have special access rights associated with his or her log-in. In this implementation, for example, the user must have a System Administrator log-in.

The Wellness Plan Maintenance screen 2300 shows the client name 2302, the patient name 2304, the type of plan 2306, and the status of the plan 2308. The client software automatically fills in this information based on the patient and client records of the selected patient. In other words, before accessing the screen, the user has already selected the client and patient. Thus, when the user accesses the screen, the client software automatically retrieves the proper data from the patient's records stored on the server.

If the client has not endorsed the plan, the status of the plan is listed as tentative. This feature is implemented by flagging the patient's file with the wellness plan information and the tentative status when the plan is selected. The wellness plan status is updated to active when the wellness plan is actually endorsed as described above.

To change information about the plan, the user can click on the "edit" button 2310 and then make the desired changes. For example, the user can change the status of the wellness plan from tentative to canceled by selecting the "canceled" status from the Contract Status list box 2308. The user can also select automatic renewal in the "Automatic Renewal" check buttons 2312–2314 displayed in the window.

To save the changes, the user selects the "Save" button 2316. In response, the client software sends a message to the server to update the patient files stored on the server. These files include the Wellness Plan Contract file and the patient file. The client file is not updated for wellness plan activity, as the client may have one pet covered and another pet not covered by a wellness plan.

The Wellness plan maintenance screen 2300 also includes a data link box 2320 that includes a check box that the user can select to instruct the client software to refer to the customer data (in this case the customer is Terrie Maas as shown in box 2302) rather than the contract purchaser data. This is useful in cases where the purchaser is different than the client. The client is usually the pet owner.

File Maintenance on the Central Computer and the Server

The server at each hospital maintains several database files that are relevant to the operation of the wellness plan software. The following table provides a list of these files and the fields contained in them. A file, in this implementation, refers to a relational database table. Each table includes a number of records corresponding to rows in the table. Each record has one or more fields corresponding to columns in the table. A link is an identifier stored in a field of a record that uniquely identifies a table related to that record.

| File | Fields | Comments |
| --- | --- | --- |
| Wellness Plan Contract Definition | Title of plan; Payment Terms; Average Daily Cost; Average Daily Savings; Monthly Payment. | This file defines the terms of a wellness plan as established by the plan administrator. There is a file for each wellness plan. The central computer maintains copies of these files and also sends copies to the server at each hospital. |
| Wellness Plan Detail | Link to Wellness Plan; Contract Definition Table; Link to Inventory Table; | Each of the records in the table relate to items that are provided under the wellness plans. These records contain the fields listed here. "Relative Sales Value" is the |

-continued

| File | Fields | Comments |
|---|---|---|
| | Item Description; Relative Sales Value; Doctor Production Value. | worth assigned to an item, not necessarily the retail price. The "Doctor Production Value" is the price of the item attributed to the selling doctor. To get the wellness plan items for a particular plan, the software relates the plan identifier with this table. |
| Wellness Plan Contract | Clinic; Customer; Pet; Plan Level; Date Initiated; Initiation Amount; Number of Payments; Payment Starting Date; Payment Amount. | This file is updated when a new contract is endorsed. One file is created for each endorsed contract. |
| Wellness Plan Items | Link to Wellness Plan; Contract File; Link to Patient Table; Link to Inventory Item; Value of how much of the; Wellness plan contract; has been delivered/still; owed to the client. | This table includes records for each wellness plan item covered under the plan. This table is created for each wellness plan. |
| Client | Name; Address; (possibly other client; contact information). | This table includes records for clients. Each record includes fields containing client contact information such as the client's name and address. |
| Patient (Pets) | Name of Breed; Species; Sex; Age; Birth date; Wellness Plan Flag; Wellness PLan Level; Plan Expiration Date. | A patient file includes patient records. Each patient record has a number of fields that provide information about a patient such as the attributes shown here. In addition, the file includes a Wellness plan indicating whether the pet is on a plan. |
| Bonus Observation | Clinic; Employee; Customer; Pet; Date; Time. | This file is updated when a wellness plan event occurs. |
| Bonuses Recorded | Employee Patient Name; Patient; Link to Wellness Plan; Contract File for the patient; Date Paid; Amount of Bonus (dollars). | This file is generated and maintained on the central computer. It is computed in the process of generating a payroll report for specifying employee bonus information to the payroll system. |
| Inventory | Item Name; Description; Retail Price; Acquisition Cost; Method of Administration; Species Specific Information. | This table is used to maintain information about product and service items provided at a clinic. |
| Accounting Sales Line Item | Item Name; Retail Price; Actual Charge to Client; Wellness Plan Value; Doctor Production Value; Item Status ("to do,; or "done"); Link to Wellness Plan; Contract File; Link to Patient Table; Link to Inventory Item. | This table is created during a patient visit to keep track of product and service items that are either provided or scheduled to be provided ("to do" status) during the visit. This table, along with the wellness plan item table, is used to compute an invoice for an office visit. |

The server computer at each hospital sends a copy of each of these files to the central computer on a periodic basis (e.g., daily). The central wellness plan administrator maintains a set of these files for all of the hospitals that it manages. When the central wellness plan administrator receives these files, it adds new records in its files for new plans and updates records based on changes recorded at the hospitals.

The central wellness plan administrator performs a variety of functions relating to the management of wellness plans, including:

1) Computation of Wellness Plan Bonuses;
2) Preparation of Payment files; and
3) Report Generation.

The central wellness plan administrator computes employee bonuses based on the wellness plan observations recorded at the hospitals and uploaded to the central computer. This feature is explained in more detail below.

The central wellness plan administrator analyzes the billing information uploaded from the hospitals and creates the files necessary to obtain payments from a client's bank account or credit card. Specifically, it creates payment files and submits them electronically to the bank. The bank makes all of the individual charges, including both credit card charges and account debits, and makes the deposit directly into the plan administrator's account.

Because the central computer captures and maintains information about the wellness plans from each hospital, it is able to generate a variety of reports. Some examples of these reports include employee earnings, current and deferred earnings (revenue report per hospital, initiation fees earned per hospital, cash received, deferred revenue, contracts valuation, cash projection, etc.), customer contracts report, expired credit cards, returned payments, renewal notices, expiring contracts, etc. The precise nature of these reports is not particularly critical to the invention, so a detailed description of them is omitted.

Employee Bonuses

There are two principal aspects to determining employee bonuses associated with the promotion of wellness plans. First, as explained above, the system tracks wellness plan observations and keeps a record of them. Second, the recorded observations are evaluated to compute the bonuses due each member of the provider team.

As explained above, the central wellness plan administrator obtains the bonus observation file from the hospital. On a periodic basis, the administrator analyzes this file and calculates employee bonuses attributable to promotion of wellness plans. The administrator computes the bonuses as follows. The administrator analyzes the bonus observation file to produce a list of bonus observations for patients associated with new wellness plan contracts. This list is filtered further so that there is at most one observation per employee for each new contract. The bonus amount for the wellness plan are computed based on the level of the wellness plans:

Level 1=10
Level 2=20
Level 3=30
Level 4=40

The administrator applies bonuses equally to the last 4 instances of client contacts, excluding duplicates. If there are fewer then 4 client contacts after duplicates are removed, then the bonuses are applied equally to these client contacts. The administrator computes a bonus per employee by dividing the bonus amount by the number of non-duplicate client contacts. It then prepares a report listing the bonuses per employee for entry into a payroll system.

Conclusion

While we have described the invention with reference to a specific implementation, we do not intend to limit the scope of the invention to this implementation. The system can be implemented in a client-server configuration, or in a single computer. In the latter case, both the client and server functions are performed on the same computer and the tables are maintained on this computer, rather than a remote server. The specific display format of the user interface screens can vary as well.

In view of the many possible embodiments to which the principles of our invention may be applied, it should be recognized that the illustrated embodiment is only a preferred example of the invention and should not be taken as a limitation on the scope of the invention. Rather, the scope of the invention is defined by the following claims. We therefore claim as our invention all that comes within the scope and spirit of these claims.

We claim:

1. A computer implemented method for managing a wellness plan comprising:

maintaining a list of wellness plan items associated with a wellness plan for a patient;

displaying a user interface for enabling a user to select among product or service items;

in response to receiving an entry of a selected product or service item in the user interface, recording the selected entry;

computing an invoice for a patient visit, checking whether the selected entry is in the wellness plan items, and if so, discounting the selected entry.

2. The method of claim 1, further including:

displaying a user interface enabling a user to select a wellness plan for a patient from among two or more wellness plan options displayed to the user, where each of the wellness plan options is associated with a set of wellness plan items; and in response to a user selecting one of the wellness plan options, creating a record of the set of wellness plan items associated with the selected wellness plan option for the patient.

3. The method of claim 1 wherein the user interface for managing a patient visit includes a series of display screens that guide the user through a medical exam and enable the user to select from among the product or service items.

4. The method of claim 1 further including:

computing a cost estimate of selected product or services items entered during the patient visit; and displaying an indicator of cost savings for the products or service items attributable to the wellness plan.

5. The method of claim 1 further including:

automatically scheduling patient visits for the patient covered by the wellness plan.

6. The method of claim 1 further including:

in response to a program action associated with promotion of a wellness plan, recording an event including a provider identifier indicating a provider associated with the event; and evaluating events to determine bonuses for providers.

7. The method of claim 6 wherein the program action comprises entry of an input to select a display of wellness plan information.

8. A wellness plan management system comprising:

a medical facility computer having a user interface for enabling a client to enter billing information and to select a wellness plan from among two or more wellness plans, each having a set of predetermined wellness plan items, the user interface further including an interactive display for selecting product or service items provided to a patient during a visit; the medical facility computer being programmed to record selected product or service items provided to the patient and to compare predetermined wellness plan items with the selected items to determine a wellness plan discount; and a remote computer in communication with the medical facility computer for obtaining the billing information and for automatically billing clients that have selected a wellness plan.

9. The system of claim 8 wherein the medical facility computer is programmed to estimate cost savings for the selected product and service items due under a wellness plan associated with the patient and is programmed to display the cost savings.

10. The system of claim 8 wherein the medical facility computer is programmed to record events associated with a promotional activity of the wellness plans, wherein the events identify an employee responsible for the promotional activity and are evaluated to compute employee bonuses.

11. A computer readable medium having software for managing a wellness plan, the software comprising instructions for:

maintaining a list of wellness plan items associated with a wellness plan for a patient;

displaying a user interface for enabling a user to select among product or service items;

in response to receiving an entry of a selected product or service item in the user interface, recording the selected entry;

computing an invoice for a patient visit, checking whether the selected entry is in the wellness plan items, and if so, discounting the selected entry.

\* \* \* \* \*